(12) United States Patent
Nakanishi et al.

(10) Patent No.: US 7,723,081 B1
(45) Date of Patent: May 25, 2010

(54) BACTERIA CONTAINING ASPARTATE-SEMIALDEHYDE DEHYDROGENASE, PHOSPHOENOLPYRUVATE CARBOXYLASE, AND TRANSHYDROGENASE TO PRODUCE L-LYSINE IN ESCHERICHIA, AND METHODS OF USING SAME

(75) Inventors: Kazuo Nakanishi, Kawasaki (JP); Yoshimi Kikuchi, Kawasaki (JP); Junichiro Kojima, Kawasaki (JP); Tomoko Suzuki, Kawasaki (JP); Yasushi Nishimura, Kawasaki (JP); Hiroyuki Kojima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/149,450

(22) PCT Filed: Jan. 21, 2000

(86) PCT No.: PCT/JP00/00298

§ 371 (c)(1),
(2), (4) Date: Jun. 27, 2002

(87) PCT Pub. No.: WO01/53459

PCT Pub. Date: Jul. 26, 2001

(51) Int. Cl.
*C12P 13/08* (2006.01)

(52) U.S. Cl. .................. 435/115; 435/252; 435/325; 435/320.1; 435/7.1

(58) Field of Classification Search ............ 435/252.33, 435/115, 252.2
See application file for complete search history.

(56) References Cited

U.S. PATENT DOCUMENTS

| | | | |
|---|---|---|---|
| 4,346,170 | A | 8/1982 | Ajinomoto |
| 5,827,698 | A | 10/1998 | Kikuchi et al. |
| 5,830,716 | A | 11/1998 | Kojima et al. |
| 5,876,983 | A | 3/1999 | Sugimoto et al. |
| 5,919,694 | A | 7/1999 | Sugimoto et al. |
| 5,932,453 | A | 8/1999 | Kikuchi et al. |
| 6,040,160 | A | 3/2000 | Kojima et al. |
| 6,200,785 | B1 * | 3/2001 | Kreutzer et al. ............. 435/115 |
| 2003/0049804 | A1 * | 3/2003 | Pompejus et al. ........... 435/115 |
| 2004/0126854 | A1 * | 7/2004 | Hanke et al. ................ 435/115 |

FOREIGN PATENT DOCUMENTS

| | | |
|---|---|---|
| DE | 38 23 451 A | 1/1990 |
| EP | 0 318 663 A1 | 6/1989 |
| EP | 0 723 011 A1 | 7/1996 |
| EP | 0 733 710 A1 | 9/1996 |
| EP | 0 733 712 A1 | 9/1996 |
| WO | 95/16042 | 6/1995 |

OTHER PUBLICATIONS

Chatterjee M. et al.,"Microbial Production of L-lysine: A Review", Hind. Antibiot. Bull., 1997, vol. 39, pp. 20-49.
Jetten, M. S. M., et al., "Recent Advances in the Physiology and Genetics of Amino Acid-Producing Bacteria," Critical Rev. Biotechnol. 1995;15(1):73-103.
Vauterni, M., et al., "Functional rescue of a bacterial dapA auxotroph with a plant cDNA library selects for mutant clones encoding a feedback-insensitive dihydrodipicolinate synthase," The Plant Journal 2000;21(3):239-248.
English translation of Third Party Letter (Degussa) to the European Patent Office concerning the patentability of the invention, dated Jul. 26, 2007, pp. 1-7.
Office Communication from EP Patent App. No. 00900872.3 (Sep. 17, 2007).

* cited by examiner

*Primary Examiner*—Hope A Robinson
(74) *Attorney, Agent, or Firm*—Shelly Guest Cermak; Cermak Kenealy Vaidya & Nakajima LLP

(57) ABSTRACT

An *Escherichia* bacterium (1) which harbors dihydrodipicolinate synthase of which feedback inhibition by L-lysine is desensitized and aspartokinase of which feedback inhibition by L-lysine is desensitized, (2) in which intracellular activity of dihydrodipicolinate reductase is enhanced, and (3) in which a diaminopimelate dehydrogenase gene is introduced or intracellular activities of tetrahydrodipicolinate succinylase and succinyl diaminopimelate deacylase are enhanced, wherein intracellular activity of aspartate-semialdehyde dehydrogenase or phosphoenolpyruvate carboxylase is enhanced, is cultured in a suitable medium to produce and accumulate L-lysine in culture, and the L-lysine is collected from the culture.

14 Claims, 20 Drawing Sheets

US 7,723,081 B1

BACTERIA CONTAINING ASPARTATE-SEMIALDEHYDE DEHYDROGENASE, PHOSPHOENOLPYRUVATE CARBOXYLASE, AND TRANSHYDROGENASE TO PRODUCE L-LYSINE IN *ESCHERICHIA*, AND METHODS OF USING SAME

TECHNICAL FIELD

The present invention relates to microbial industries. More specifically, the present invention relates to a method for producing L-lysine by fermentation, and a microorganism used for the production method.

BACKGROUND ART

In the production of L-lysine by fermentation, strains isolated from nature or artificial mutants thereof have conventionally been used in order to improve the productivity. Many artificial mutant strains that produce L-lysine are known, and many of them are S-2-aminoethylcysteine (AEC) resistant strains and belong to the genus *Brevibacterium, Corynebacterium, Bacillus* or *Escherichia*. Further, various techniques have been disclosed for increasing the amino acid production, for example, use of a transformant obtained by using recombinant DNA.

As for *Escherichia* bacteria, for example, methods for producing L-lysine by using a strain in which dihydrodipicolinate synthase (DDPS) activity is enhanced have been disclosed in Japanese Patent Application Laid-open (Kokai) No. 56-18596, U.S. Pat. No. 4,346,170 and Applied Microbiology and Biotechnology, 15, pp. 227-331 (1982). Further, a method for producing L-lysine by using an *Escherichia* bacterium into which DDPS derived form a *Corynebacterium* bacterium is introduced has been disclosed in Korean Patent Publication No. 92-8382. Furthermore, a method for producing L-lysine using a strain which is transformed with a plasmid containing DNA that codes for dihydrodipicolinate synthase derived from an *Escherichia* bacterium having a mutation for desensitizing feedback inhibition by L-lysine, DNA that codes for aspartokinase of which feedback inhibition by L-lysine is desensitized, DNA that codes for dihydrodipicolinate reductase, and DNA that codes for diaminopimelate dehydrogenase derived from a coryneform bacterium is disclosed in International Publication No. WO95/16042.

As for *Brevibacterium* bacteria, International Publication No. WO95/11985 discloses that L-lysine productivity can be improved by enhancement of the activity of intracellular nicotinamide adenine dinucleotide transhydrogenase. Further, a method for producing L-lysine using a strain in which phosphoenolpyruvate carboxylase activity is solely enhanced and a method for producing L-lysine using a strain in which aspartate-semialdehyde dehydrogenase activity is solely enhanced are disclosed in Japanese Patent Application Laid-open No. 60-87788 and Japanese Patent Publication (Kokoku) No. 6-102028, respectively.

In the industrial production of amino acids by fermentation, the production is performed in a large scale. Therefore, even improvement in the yield of several percents may provide significant industrial value, and thus improvement of the yield is desired irrespective of the degree of the improvement.

DISCLOSURE OF THE INVENTION

An object of the present invention is to provide an improved method for producing L-lysine by fermentation compared with the conventional methods.

The present inventors assiduously studied in order to achieve the aforementioned object. As a result, they found that, if activity of aspartate-semialdehyde dehydrogenase or phosphoenolpyruvate carboxylase was enhanced in an *Escherichia* bacterium having a specified property, and if activity or activities of a specific enzyme or enzymes were enhanced in addition to the aforementioned enzymes in such an *Escherichia* bacterium, the productivity of the bacterium for L-lysine could be improved, and they accomplished the present invention based on these findings.

That is, the present invention provides:

in a first aspect, an *Escherichia* bacterium in which (1) intracellular activities of dihydrodipicolinate synthase, aspartokinase and dihydrodipicolinate reductase are enhanced, and (2) intracellular activity of diaminopimelate dehydrogenase or intracellular activities of tetrahydrodipicolinate succinylase and succinyl diaminopimelate deacylase is/are enhanced, wherein intracellular activity of aspartate-semialdehyde dehydrogenase or phosphoenolpyruvate carboxylase is enhanced;

in a second aspect, an *Escherichia* bacterium in which (1) intracellular activities of dihydrodipicolinate synthase, aspartokinase and dihydrodipicolinate reductase are enhanced, and (2) intracellular activity of diaminopimelate dehydrogenase or intracellular activities of tetrahydrodipicolinate succinylase and succinyl diaminopimelate deacylase is/are enhanced, wherein intracellular activity of phosphoenolpyruvate carboxylase and intracellular activity of nicotinamide adenine dinucleotide transhydrogenase or aspartate-semialdehyde dehydrogenase are enhanced; and in a third aspect, an *Escherichia* bacterium in which (1) intracellular activities of dihydrodipicolinate synthase, aspartokinase and dihydrodipicolinate reductase are enhanced, and (2) intracellular activity of diaminopimelate dehydrogenase or intracellular activities of tetrahydrodipicolinate succinylase and succinyl diaminopimelate deacylase is/are enhanced, wherein intracellular activities of phosphoenolpyruvate carboxylase and nicotinamide adenine dinucleotide transhydrogenase and intracellular activity of aspartate-semialdehyde dehydrogenase or aspartase are enhanced (hereinafter, the bacteria according to the aforementioned three aspects are also collectively referred to as the "bacteria of the present invention").

In the bacteria of the present invention, it is preferred that the intracellular activities of aspartate-semialdehyde dehydrogenase and aspartase are enhanced.

Further, in the bacteria of the present invention, it is preferred that aspartokinase, dihydrodipicolinate reductase, tetrahydrodipicolinate succinylase, succinyl diaminopimelate deacylase, phosphoenolpyruvate carboxylase and aspartate-semialdehyde dehydrogenase are each derived from an *Escherichia* bacterium, nicotinamide adenine dinucleotide transhydrogenase and aspartase, if present, are each derived from an *Escherichia* bacterium, dihydrodipicolinate synthase is derived from an *Escherichia* bacterium or a *Brevibacterium* bacterium, and diaminopimelate dehydrogenase is derived from a *Brevibacterium* bacterium.

In the bacteria of the present invention, it is preferred that intracellular activity of enzyme of which intracellular activity is enhanced, is enhanced by one of the following items or any combination thereof.

(1) Introduction of a plasmid having a gene of the enzyme.

(2) Increase of copy number of a gene of the enzyme on chromosome.

(3) Modification of a promoter sequence of a gene of the enzyme on chromosome.

Furthermore, in the bacteria of the present invention, it is preferred that the intracellular activities of dihydrodipicolinate synthase and aspartokinase are enhanced by harboring dihydrodipicolinate synthase of which feedback inhibition by L-lysine is desensitized and aspartokinase of which feedback inhibition by L-lysine is desensitized, and the intracellular activity of diaminopimelate dehydrogenase is enhanced by introduction of a diaminopimelate dehydrogenase gene.

The present invention also provides a method for producing L-lysine, which comprises culturing any of the bacteria of the present invention in a suitable medium to produce and accumulate L-lysine in the culture, and collecting the L-lysine from the culture (hereinafter also referred to as the "production method of the present invention").

BEST MODE FOR CARRYING OUT THE INVENTION

<1> Bacteria of the Present Invention

Figure 1:
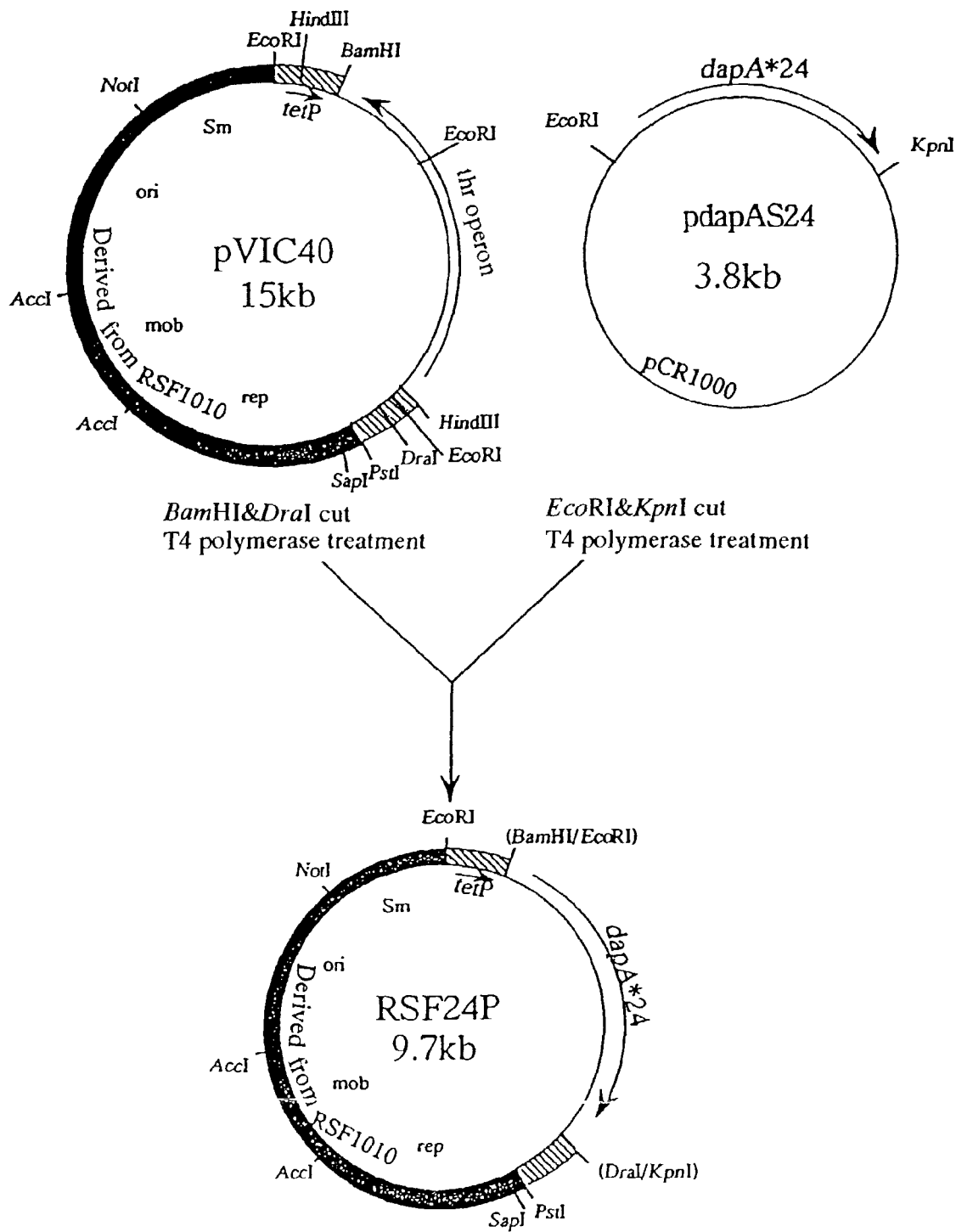
FIG. 1 shows a production process of plasmid RSF24P derived from RSF1010, which contains dapA*24.

The bacteria of the present invention are *Escherichia* bacteria in which (1) intracellular activities of dihydrodipicolinate synthase, aspartokinase and dihydrodipicolinate reductase are enhanced, and (2) intracellular activity of diaminopimelate dehydrogenase, or intracellular activities of tetrahydrodipicolinate succinylase and succinyl diaminopimelate deacylase is/are enhanced, and the intracellular activities of the following enzymes are further enhanced:

(1) aspartate-semialdehyde dehydrogenase or phosphoenolpyruvate carboxylase, (2) phosphoenolpyruvate carboxylase, and nicotinamide adenine dinucleotide transhydrogenase (hereinafter also referred to as "transhydrogenase") or aspartate-semialdehyde dehydrogenase, or (3) phosphoenolpyruvate carboxylase and transhydrogenase, and aspartate-semialdehyde dehydrogenase or aspartase.

The bacteria of the present invention are preferably *Escherichia* bacteria in which intracellular activities of phosphoenolpyruvate carboxylase, transhydrogenase, aspartate-semialdehyde dehydrogenase and aspartase are further enhanced.

The bacteria of the present invention preferably belong to *Escherichia coli* (*E. coli*).

In this specification, the expression of "intracellular activity is enhanced" means that the intracellular enzymatic activity is increased compared with a wild strain (for example, *E. coli* W3110 strain) or a parent strain (strain in which intracellular activities of all of the enzymes included in the combinations specified in the present invention are not enhanced), and also means that a bacterium has an enzymatic activity that is not possessed by a wild strain or a parent strain. The measurement methods for the activities of the aforementioned enzymes are known, and enhancement of the intracellular activities can be easily confirmed by those skilled in the art.

Means of enhancing the intracellular activities includes the following means and combinations thereof, but is not limited to these.

First of all, means of increasing expression amount of the enzymes can be mentioned.

Specifically, as means of increasing the expression amount of enzymes, the following means can be mentioned.

(1) Introduction of Plasmid Containing Gene of Enzyme

As the plasmid, a vector autonomously replicable in an *Escherichia* bacterium cell can be used. It can be introduced in a known manner. That is, a gene of interest can be inserted into the vector and an *Escherichia* bacterium can be transformed with that vector. This vector is preferably a multi-copy type plasmid.

The genes may be carried by the same plasmid or different plasmids. Some of the genes may be carried by the same plasmid. When two or more kinds of plasmids are used, it is preferable to use plasmids that have stable partitioning systems that enable stable co-existence of these plasmids in a cell. The order of introduction of the genes is not particularly, limited.

(2) Increase of Copy Number of Gene of Enzyme on Chromosome

The copy number can be increased by amplifying DNA on chromosome DNA using Mu phage or the like.

DNA on chromosome DNA may be one originally possessed by *Escherichia* bacteria, or one incorporated into chromosome of a host microorganism by a method using transduction, transposon (Berg, D. E. and Berg C. M., Bio/Technol., 1, 417 (1983)), Mu phage (Japanese Patent Application Laid-open No. 2-109985) or homologous recombination (Experiments in Molecular Genetics and Cold Spring Harbor Lab. (1972)).

(3) Modification of Promoter Sequence of Gene of Enzyme

A promoter sequence can be modified to increase transcription amount of a gene and thereby increase the expression amount. For example, a promoter can be enhanced by introducing a mutation into the promoter to increase the transcription amount of a gene located downstream from the promoter. Other than introducing a mutation into the promoter, a promoter that can function in *Escherichia* bacteria such as lac, trp, tac, trc and PL may be newly introduced. Alternatively, transcription amount of gene can be increased by newly introducing an enhancer. Although the promoter sequence may be one for a gene of the enzyme on chromosome or one for a gene of the enzyme on a plasmid, it is preferably one for gene of the enzyme on chromosome. The introduction of genes such as promoters into chromosome DNA is described in Japanese Patent Application Laid-open No. 1-215280, for example.

The origins of the genes for the aforementioned enzymes are not particularly limited, and those obtained from various origins may be used so long as the genes can be expressed and the genetic products can function in *Escherichia* bacteria.

Hereafter, methods for obtaining L-lysine biosynthesis system genes and transhydrogenase gene of *E. coli*, and dihydrodipicolinate synthase and diaminopimelate dehydrogenase genes of *Brevibacterium lactofermentum* will be exemplified.

A phosphoenolpyruvate carboxylase gene (ppc) can be obtained from the plasmid pS2 (Sabe, H. et al., Gene, 31, 279 (1984)) or pT2, which contain this gene. A DNA fragment that contains ppc can be obtained by digesting pS2 with AatII and AflII. Further, a DNA fragment that contains ppc can also be obtained by digesting pT2 with SmaI and ScaI. An *E. coli* F15 strain harboring pT2 (AJ12873) was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Jul. 15, 1993, and received an accession number of FERM P-13752. Then, it was transferred to an international deposition under the provisions of the Budapest Treaty on Jul. 11, 1994, and received an accession number of FERM BP-4732.

An aspartokinase gene (lysC) can be obtained by amplification by PCR using *E. coli* chromosome DNA as a template and two kinds of oligonucleotide primers prepared based on the known nucleotide sequence of lysC (Cassan, M., Parsot, C., Cohen, G. N., and Patte, J. C., J. Biol. Chem., 261, 1052 (1986) (for example, those mentioned in International Publication No. WO95/16042, SEQ ID NOS: 5 and 6).

An aspartate-semialdehyde dehydrogenase gene (asd) can be obtained from the plasmid pAD20 (Haziza, C. et al., EMBO, 1, 379 (1982)), which contains this gene. If pAD20 is digested with AseI and ClaI, a DNA fragment containing asd will be obtained.

A dihydrodipicolinate synthase gene (dapA) can be obtained by amplification by PCR using *E. coli* chromosome DNA as a template and two kinds of oligonucleotide primers (for example, those of SEQ ID NOS: 1 and 2 mentioned in International Publication No. WO95/16042) prepared based on the known nucleotide sequence of dapA (Richaud, F. et al., J. Bacteriol., 297 (1986)).

A dihydrodipicolinate reductase gene (dapB) can be obtained by amplification by PCR using *E. coli* chromosome DNA as a template and two kinds of oligonucleotide primers (for example, those of SEQ ID NOS: 9 and 10 mentioned in International Publication No. WO95/16042) prepared based on the known nucleotide sequence of dapB (Bouvier, J. et al., J. Biol. Chem., 259, 14829 (1984)).

A tetrahydrodipicolinate succinylase gene (dapD) can be obtained by amplification by PCR using *E. coli* chromosome DNA as a template and two kinds of oligonucleotide primers (for example, those of SEQ ID NOS: 15 and 16 mentioned in International Publication No. WO95/16042) prepared based on the known nucleotide sequence of dapD (Richaud, C. et al., J. Biol. Chem., 259, 14824 (1984)).

A succinyl diaminopimelate deacylase gene (dapE) can be obtained by amplification by PCR using *E. coli* chromosome DNA as a template and two kinds of oligonucleotide primers (for example, those of SEQ ID NOS: 17 and 18 mentioned in International Publication No. WO95/16042) prepared based on the known nucleotide sequence of dapE (Bouvier, J. et al., J. Bacteriol., 174, 5265 (1992)).

An aspartase gene (aspA) can be obtained by amplification by PCR using *E. coli* chromosome DNA as a template and two kinds of oligonucleotide primers (for example, those of SEQ ID NOS: 5 and 6 mentioned in Sequence Listing of the present specification) prepared based on the known nucleotide sequence of aspA (Woods, S. A. et al., Biochem. J., 237 (2), 547-557 (1986)).

A transhydrogenase gene (pntAB) can be prepared based on the known nucleotide sequence of transhydrogenase gene (D. M. Clarke et al., Eur. J. Biochem., 158, 647-653 (1986)). In *E. coli*, transhydrogenase is composed of two subunits, which are encoded by pntA and pntB, respectively (D. M. Clarke et al., supra). Therefore, the both genes are prepared (see, for example, International Publication No. WO95/11985).

It can also be obtained from a plasmid containing pntAB. As the plasmid containing pntAB, the plasmid pMW::THY mentioned in International Publication No. WO95/11985 can be mentioned. This plasmid is a recombinant plasmid obtained by ligating a 3.0 kb DNA fragment of *E. coli* K-12 MC1061 strain, which contains pntA and pntB, and a BamHI and HindIII fragment of the plasmid vector pMW118. An *Escherichia coli* JM109 strain harboring pMW::THY was designated as AJ12929 strain, and deposited at the National Institute of Bioscience and Human-Technology, Agency of Industrial Science and Technology, Ministry of International Trade and Industry (postal code 305-0046, 1-3 Higashi 1-chome, Tsukuba-shi, Ibaraki-ken, Japan) on Oct. 4, 1993, and received an accession number of FERM P-13890. Then, it was transferred to an international deposition under the provisions of the Budapest Treaty on Sep. 11, 1994, and received an accession number of FERM BP-4798.

A dihydrodipicolinate synthase gene (dapA) of *Brevibacterium lactofermentum* can be obtained by amplification by PCR using chromosome DNA of *Brevibacterium lactofermentum* as a template and two kinds of oligonucleotide primers (for example, those of SEQ ID NOS: 3 and 4 mentioned in Sequence Listing of the present specification) prepared based on the known nucleotide sequence of dapA (Bonassie, S. et al., N.A.R., 18 (21), 6421 (1990)).

A diaminopimelate dehydrogenase gene (ddh) of *Brevibacterium lactofermentum* can be obtained by amplification by PCR using chromosome DNA of *Brevibacterium lactofermentum* as a template and two kinds of oligonucleotide primers (for example, those of SEQ ID NOS: 11 and 12 mentioned in International Publication No. WO95/16042) prepared based on the known nucleotide sequence of ddh of *Corynebacterium glutamicum* (Ishino, S. et al., Nucleic Acids Res., 15, 3917 (1987)).

As the means of enhancing the intracellular activities, there can also be mentioned means of increasing specific activities of the enzymes. This means may be combined with the means of increasing the expression amounts of the enzymes.

As means of increasing specific activities of the enzymes, there can be mentioned introduction of an enzyme having a mutation for increasing specific activity, inclusion of an enzyme of which feedback inhibition is desensitized, when the enzyme receives feedback inhibition, and so forth.

Examples of the enzyme of which feedback inhibition is desensitized include dihydrodipicolinate synthase (DDPS) of which feedback inhibition by L-lysine is desensitized and aspartokinase (AK) of which feedback inhibition by L-lysine is desensitized.

The expression that "feedback inhibition by L-lysine is desensitized" means that substantial desensitization of the inhibition is sufficient, and it is not required that the inhibition should be completely desensitized. Further, an enzyme derived from an organism other than *Escherichia* bacteria is also included in the enzyme of which feedback inhibition by L-lysine is desensitized, irrespective of whether it is a wild-type or mutant type enzyme of the organism, if degree of the feedback inhibition by L-lysine is lower than that of a wild-type enzyme derived from an *Escherichia* bacterium. Therefore, an enzyme that is originally free from the feedback inhibition by L-lysine such as DDPS derived from *Brevibacterium* bacteria is also included.

The degree of the feedback inhibition by L-lysine can be evaluated by known methods such as the methods described in International Publication No. WO95/16042, Examples 1 and 2.

As DDPS of which feedback inhibition by L-lysine is desensitized (desensitized DDPS) and AK of which feedback inhibition by L-lysine is desensitized (desensitized AK), those disclosed in International Publication No. WO95/16042 and Japanese Patent Application Laid-open No. 10-113183 can be mentioned.

That is, examples of the desensitized DDPS include those having a mutation desensitizing the feedback inhibition by L-lysine found in wild-type DDPS. As the wild-type DDPS, those derived from *Escherichia* bacteria, especially DDPS derived from *E. coli*, can be mentioned. Examples of the mutation that desensitizes the feedback inhibition by L-lysine of DDPS include:

(1) mutation for replacing an amino acid residue corresponding to the alanine residue at position 81 with another amino acid residue (preferably valine residue), (2) mutation for replacing an amino acid residue corresponding to the histidine residue at position 118 with another amino acid residue (preferably tyrosine residue), and (3) mutation for replacing an amino acid residue corresponding to the alanine residue at position 81 with another amino acid residue (preferably valine residue), and replacing an amino acid residue corresponding to the histidine residue at position 118 with another amino acid residue (preferably tyrosine residue) in the DDPS amino acid sequence shown as SEQ ID NO: 4 in International Publication No. WO95/16042 wherein the position is counted from N-terminus of DDPS. It is well known that difference in amino acid sequence that does not affect activity may occur among species or strains, and an amino acid residue corresponding to the aforementioned specific amino acid residues can be easily recognized by those skilled in the art.

Other examples of the desensitized DDPS include DDPS derived from coryneform bacteria, for example, *Brevibacterium lactofermentum* (Cremer J. et al., J. Gen. Microbiol., 134, 3221-3229 (1988)).

In order to make a desensitized DDPS to be harbored by *Escherichia* bacteria, for example, DNA that encodes the desensitized DDPS can be introduced.

Examples of the DNA coding for desensitized DDPS include those corresponding to DNA coding for a wild-type DDPS having a mutation for desensitizing the feedback inhibition by L-lysine of the encoded DDPS.

Hereafter, a method for obtaining DNA coding for desensitized DDPS (desensitized DDPS gene) will be explained by exemplifying DDPS derived from *Escherichia* bacteria. As for DDPS of other organisms, DNA can be obtained similarly. Further, if a wild-type DDPS derived from another organism is a desensitized DDPS, DNA coding for it can be used as it is.

The DNA coding for wild-type DDPS is not particularly limited so long as it codes for DDPS derived from an *Escherichia* bacterium. Specifically, DNA coding for the amino acid sequence shown in International Publication No. WO95/16042, SEQ ID NO: 4, can be mentioned. More specifically, there can be mentioned the sequence represented by the nucleotide numbers 272-1147 within the nucleotide sequence shown in SEQ ID NO: 3 of the same. In these sequences, one having a mutation of nucleotide sequence causing replacement of the aforementioned amino acid residues is DNA coding for a desensitized DDPS. In addition, type of the codon corresponding to the replaced amino acid residue is not particularly limited, so long as it codes for the amino acid residue. Further, it is also expected that there is slight difference in the amino acid sequence of contained DDPS among bacterial species and strains. However, those having such difference causing replacement, deletion or insertion of amino acid residues at positions that do not affect the activity of enzyme fall within the scope of the desensitized DDPS gene.

Such a desensitized DDPS gene can be obtained, for example, as follows. First, DNA containing a wild-type DDPS gene or another DDPS gene having a mutation is subjected to an in vitro mutation treatment, and the DNA undergone the mutation treatment and a vector DNA compatible with a host are ligated to prepare a recombinant DNA. The recombinant DNA is introduced into host microorganisms to obtain transformants, and a transformant that becomes to express a desensitized DDPS is selected from the transformants. Such a transformant harbors the desensitized DDPS gene. Alternatively, DNA containing a wild-type DDPS gene or another DDPS gene having a mutation and a vector DNA compatible with a host may be ligated to prepare a recombinant DNA. Then, the recombinant DNA can be subjected to an in vitro mutation treatment, and introduced into host microorganisms to obtain transformants, and a transformant that becomes to express a desensitized DDPS can be selected from the transformants. Such a transformant also harbors the desensitized DDPS gene.

Furthermore, a microorganism that produces a wild-type DDPS may be subjected to a mutation treatment to prepare a mutant strain that produces a desensitized DDPS, and then a desensitized DDPS gene can be obtained from the mutant strain. Alternatively, if a transformant into which a recombinant DNA ligated with a wild-type gene is introduced is subjected to a mutation treatment to prepare a mutant strain producing a desensitized DDPS and then a recombinant DNA is collected from the mutant strain, a desensitized DDPS gene is created on that DNA.

Examples of agents for the in vitro mutation treatment of DNA include hydroxylamine and so forth. Hydroxylamine is a chemical mutation treatment agent that causes replacement of cytosine with thymine by changing cytosine into $N^4$-hydroxycytosine. When a microorganism itself is subjected to a mutation treatment, the treatment is performed with ultraviolet irradiation or a mutagenizing agent usually used for artificial mutation such as N-methyl-N'-nitro-N-nitrosoguanidine (NTG) and nitrous acid.

As a bacterium donating the DNA containing a wild-type DDPS gene or another DDPS gene containing a mutation, any of microorganisms belonging to the genus *Escherichia* may be used. Specifically, those mentioned in the literature of Neidhardt et al. (Neidhardt, F. C. et. al., *Escherichia coli* and *Salmonella Typhimurium*, American Society for Microbiology, Washington D.C., 1208, Table 1) can be used. For example, *E. coli* JM109 strain and MC1061 strain can be mentioned. When a wild strain is used as a donor of DNA containing a DDPS gene, DNA containing a wild-type DDPS gene can be obtained.

Examples of the desensitized AK include those having a mutation desensitizing the feedback inhibition by L-lysine found in wild-type AK. As the wild-type AK, those derived from *Escherichia* bacteria, especially aspartokinase III (AKIII) derived from *E. coli*, can be mentioned. Examples of the mutation that desensitizes the feedback inhibition by L-lysine of AKIII include:

(a) mutation for replacing an amino acid residue corresponding to the glycine residue at position 323 with another amino acid residue (preferably aspartic acid residue), (b) mutation for replacing an amino acid residue corresponding to the glycine residue at position 323 with another amino acid residue (preferably aspartic acid residue), and replacing an amino acid residue corresponding to the glycine residue at position 408 with another amino acid residue (preferably aspartic acid residue), (c) mutation for replacing an amino acid residue corresponding to the arginine residue at position 34 with another amino acid residue (preferably cysteine residue), and replacing an amino acid residue corresponding to the glycine residue at position 323 with another amino acid residue (preferably aspartic acid residue), (d) mutation for replacing an amino acid residue corresponding to the leucine residue at position 325 with another amino acid residue (preferably phenylalanine residue), (e) mutation for replacing an amino acid residue corresponding to the methionine residue at position 318 with another amino acid residue (preferably isoleucine residue), (f) mutation for replacing an amino acid residue corresponding to the methionine residue at position 318 with another amino acid residue (preferably isoleucine residue), and replacing an amino acid residue corresponding to the valine residue at position 349 with another amino acid residue (preferably methionine residue), (g) mutation for replacing an amino acid residue corresponding to the serine residue at position 345 with another amino acid residue (preferably leucine residue), (h) mutation for replacing an amino acid residue corresponding to the valine residue at position 347 with another amino acid residue (preferably methionine residue), (i) mutation for replacing an amino acid residue corresponding to the threonine residue at position 352 with another amino acid residue (preferably isoleucine residue), (j) mutation for replacing an amino acid residue corresponding to the threonine residue at position 352 with another amino acid residue (preferably isoleucine residue), and replacing an amino acid residue corresponding to the serine residue at position 369 with another amino acid residue (preferably phenylalanine residue), (k) mutation for replacing an amino acid residue corresponding to the glutamic acid residue at position 164 with another amino acid residue (preferably lysine residue), and (l) mutation for replacing an amino acid residue corresponding to the methionine residue at position 417 with another amino acid residue (preferably isoleucine residue), and replacing an amino acid residue corresponding to the cysteine residue at position 419 with another amino acid residue (preferably tyrosine residue) in the AKIII amino acid sequence shown as SEQ ID NO: 8 in International Publication No. WO95/16042 wherein the position is counted from the N-terminus of AKIII. Further, there can be mentioned a mutation for replacing an amino acid residue corresponding to the glycine residue at position 323 with another amino acid residue corresponding to the methionine residue at position 318 with another amino acid residue (preferably isoleucine residue) (Japanese Patent Application Laid-open No. 10-113183). It is well known that difference in amino acid sequence that does not affect activity may occur among species or strains, and an amino acid residue corresponding to the aforementioned specific amino acid residues can be easily recognized by those skilled in the art.

Other examples of the desensitized AK include mutant type AK derived from coryneform bacteria (Japanese Patent Application Laid-open No. 6-62866).

In order to make a desensitized AK to be harbored by *Escherichia* bacteria, for example, DNA that encodes the desensitized AK can be introduced into the *Escherichia* bacteria.

Examples of the DNA coding for a desensitized AK include those corresponding to a DNA coding for a wild-type AK having a mutation for desensitizing the feedback inhibition by L-lysine for the encoded AK.

Hereafter, a method for obtaining DNA coding for a desensitized AK will be explained by exemplifying AKIII derived from *Escherichia* bacteria. As also for AK of other organisms, DNA can be obtained similarly. Further, if a wild-type AK derived from another organism is a desensitized AK, DNA coding for it can be used as it is.

The DNA coding for wild-type AKIII is not particularly limited. For example, DNA coding for AKIII derived from an *Escherichia* bacterium, especially *E. coli*, can be mentioned. Specifically, DNA coding for the amino acid sequence shown in International Publication No. WO95/16042, SEQ ID NO: 8, and the sequence represented by the nucleotide numbers 584-1930 within the nucleotide sequence of SEQ ID NO: 7 in the same can be mentioned. AKIII of *E. coli* is encoded by lysC gene.

Among these sequences, one having a mutation causing replacement of the aforementioned amino acid residues is DNA coding for a mutant type AKIII. In addition, the type of the codon corresponding to the replaced amino acid residue is not particularly limited, so long as it codes for the amino acid residue. Further, it is also expected that there is slight difference in the amino acid sequence of contained AKIII among bacterial species and strains. However, those having such difference causing replacement, deletion or insertion of amino acid residues at positions that do not affect the activity of enzyme fall within the scope of the mutant AKIII gene. For example, the nucleotide sequence of the wild-type lysC gene obtained in Example 2 mentioned hereinafter (International Publication No. WO95/16042, SEQ ID NO: 7) has differences in the sequence at 6 positions with respect to the already published nucleotide sequence of lysC of *E. coli* K-12 JC411 strain (Cassan M., Parsot, C., Cohen, G. N., and Patte, J. C., J. Biol. Chem., 261, 1052 (1986)), among which two of the differences provide different encoded amino acid residues (lysC of the JC411 strain provides replacement of the glycine residue at position 58 with a cysteine residue and replacement of the glycine residue at position 401 with an alanine residue in the amino acid sequence encoded by lysC shown in SEQ ID NO: 8 of International Publication No. WO95/16042 wherein the position is counted from the N-terminus thereof). It is expected that even lysC having the same sequence as lysC of the *E. coli* K-12 JC411 strain may provide lysC having a mutation that desensitizes the feedback inhibition by L-lysine, if it is introduced any of mutations mentioned in the above (a) to (l), or a mutation for replacing an amino acid residue corresponding to the glycine residue at position 323 with another amino acid residue (preferably aspartic acid residue), and replacing an amino acid residue corresponding to the methionine residue at position 318 with another amino acid residue.

Such DNA coding for a mutant type AKIII of which feedback inhibition by L-lysine is desensitized can be obtained, for example, as follows. First, DNA containing a wild-type AKIII gene or another AKIII gene having a mutation is subjected to an in vitro mutation treatment, and the DNA undergone the mutation treatment and a vector DNA compatible with a host are ligated to prepare a recombinant DNA. The recombinant DNA can be introduced into host microorganisms to obtain transformants, and a transformant that becomes to express a mutant type AKIII can be selected from the transformants. Such a transformant harbors the mutant type gene. Alternatively, DNA containing a wild-type AKIII gene or another AKIII gene having a mutation and a vector DNA compatible with a host may be ligated to prepare a recombinant DNA. Then, the recombinant DNA can be subjected to an in vitro mutation treatment, and introduced into host microorganisms to obtain transformants, and a transformant that becomes to express a mutant type AKIII can be selected from the transformants. Such a transformant also harbors the mutant type gene.

Furthermore, a microorganism that produces a wild-type enzyme may be subjected to a mutation treatment to prepare a mutant strain that produces a mutant type enzyme, and then a mutant type gene can be obtained from the mutant strain. Examples of agents for directly subjecting DNA to a mutation treatment include hydroxylamine and so forth. Hydroxylamine is a chemical mutation treatment agent that causes replacement of cytosine with thymine by changing cytosine into $N^4$-hydroxycytosine. When a microorganism itself is subjected to a mutation treatment, the treatment is performed with ultraviolet irradiation or a mutagenizing agent usually used for artificial mutation such as N-methyl-N'-nitro-N-nitrosoguanidine (NTG).

As a bacterium donating the DNA containing a wild-type AKIII gene or another AKIII gene having a mutation, any of microorganisms belonging to the genus *Escherichia* may be used. Specifically, those mentioned in the literature of Neidhardt et al. (Neidhardt, F. C. et. al., *Escherichia coli* and *Salmonella Typhimurium*, American Society for Microbiology, Washington D.C., 1208, Table 1) can be used. For example, *E. coli* JM109 strain, MC1061 strain and so forth can be mentioned.

In the bacteria of the present invention, it is preferred that aspartokinase, dihydrodipicolinate reductase, tetrahydrodipicolinate succinylase, succinyl diaminopimelate deacylase, phosphoenolpyruvate carboxylase and aspartate-semialdehyde dehydrogenase are each derived from *Escherichia* bacteria, nicotinamide adenine dinucleotide transhydrogenase and aspartase, if present, are each derived from *Escherichia* bacteria, dihydrodipicolinate synthase is derived from an *Escherichia* bacterium or *Brevibacterium* bacterium, and diaminopimelate dehydrogenase is derived from a *Brevibacterium* bacterium.

Examples of the *Brevibacterium* bacteria include, besides *Brevibacterium lactofermentum*, *Brevibacterium flavum*, *Brevibacterium divaricatum*, *Corynebacterium glutamicum*, *Corynebacterium lilium* and so forth.

Furthermore, in the bacteria of the present invention, it is preferred that the intracellular activities of dihydrodipicolinate synthase and aspartokinase are enhanced by inclusion of dihydrodipicolinate synthase of which feedback inhibition by L-lysine is desensitized and aspartokinase of which feedback inhibition by L-lysine is desensitized, and the intracellular activity of diaminopimelate dehydrogenase is enhanced by introduction of a diaminopimelate dehydrogenase gene. Such preferred bacteria of the present invention may be obtained by introducing the plasmid pCABD2 or pCABDE1 mentioned in International Publication No. WO95/16042 into an *Escherichia* bacterium.

<2> Production Method of the Present Invention

L-Lysine can efficiently be produced by culturing the bacteria of the present invention obtained as described above in a suitable medium to produce and accumulate L-lysine in the culture, and collecting the L-lysine from the culture.

The medium used for the culture of the bacteria according to the present invention may be a usual medium containing a carbon source, a nitrogen source, inorganic ions, and other organic trace nutrients as required.

As the carbon source, it is possible to use sugars such as glucose, lactose, galactose, fructose and starch hydrolysate; alcohols such as glycerol and sorbitol; or organic acids such as fumaric acid, citric acid and succinic acid.

As the nitrogen source, it is possible to use inorganic ammonium salts such as ammonium sulfate, ammonium chloride or ammonium phosphate; organic nitrogen such as soybean hydrolysate; ammonia gas; or aqueous ammonia.

As for the organic trace nutrients, it is preferable to add required substances such as vitamin B1 and L-isoleucine, yeast extract and so forth in a suitable amount. In addition to these, a small amount of potassium phosphate, magnesium sulfate, iron ions, manganese ions and so forth are added.

Culture is preferably carried out under an aerobic condition for 16-72 hours. The culture temperature may be controlled to be 20° C. to 45° C., and pH may be controlled to be 5 to 8 during the culture. Inorganic or organic, acidic or alkaline substances as well as ammonia gas and so forth can be used for pH adjustment.

Collection of L-lysine from fermented liquor is usually carried out by a combination of an ion exchange resin method, a precipitation method and other known techniques.

EXAMPLES

The present invention will be further specifically explained hereinafter with reference to the following examples.

Example 1

<1> Preparation of *Escherichia* Bacteria Having Various Properties

The plasmids shown below were introduced into *E. coli* W3110 (tyrA).

| Name of plasmid | Contained gene |
|---|---|
| RSF24P | dapA* |
| RSFD80 | dapA*, lysC* |
| pCAB1 | dapA*, lysC*, dapB |
| pCABD2 | dapA*, lysC*, dapB, ddh |
| pCABD(B) | Brev. dapA, lysC*, dapB, ddh |
| pCABDE1 | dapA*, lysC*, dapB, dapD, dapE |

The abbreviations used for the genes have the following meanings.

ppc: Phosphoenolpyruvate carboxylase lysC: Aspartokinase III lysC*: Aspartokinase III desensitized to inhibition asd: Aspartate-semialdehyde dehydrogenase dapA: Dihydrodipicolinate synthase dapA*: Dihydrodipicolinate synthase desensitized to inhibition Brev. dapA: Dihydrodipicolinate synthase desensitized to inhibition (derived from *Brevibacterium lactofermentum*)

dapB: Dihydrodipicolinate reductase dapD: Tetrahydrodipicolinate succinylase dapE: Succinyl diaminopimelate deacylase ddh: Diaminopimelate dehydrogenase (derived from *Brevibacterium lactofermentum*)

The plasmids RSF24P, RSFD80, pCAB1, pCABD2 and pCABDE1 are described in International Publication No. WO95/16042. The constructions thereof are also described in International Publication No. WO95/16042, and outlined below.

(1) RSF24P

Based on the known dapA nucleotide sequence of *E. coli* (J. Bacteriol., 166, 297 (1986)), a fragment containing the SD sequence and open reading frame (ORF) of dapA was amplified by PCR. The amplified fragment was ligated to a cloning vector pCR1000 to obtain a plasmid pdapA2, in which dapA was ligated so that the transcription direction of dapA was reverse to the transcription direction by the lacZ promoter in pCR1000. The plasmid pdapA2 was subjected to a mutagenesis treatment by using hydroxylamine, and pdapA2 subjected to the mutagenesis treatment was introduced into *E. coli* W3110. From the transformants, those exhibiting AEC resistance were selected. Furthermore, degree of the inhibition by L-lysine of DDPS encoded by the plasmids harbored by the selected resistant strains was measured, and a strain which was desensitized to the inhibition by L-lysine was selected. The plasmid pdapA24, which was confirmed to have change of 597th C to T by sequencing, was ligated to pVIC40 at a position downstream from the tetracycline resistance gene promoter to obtain RSF24P (FIG. 1).

An *E. coli* JM109 strain into which RSF24P was introduced was designated as AJ12395, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 28, 1993 and received an accession number of FERM P-13935. Then, it was transferred to an international deposition under the provisions of the Budapest Treaty on Nov. 1, 1994, and received an accession number of FERM BP-4858.

(2) RSFD80

Figure 2:
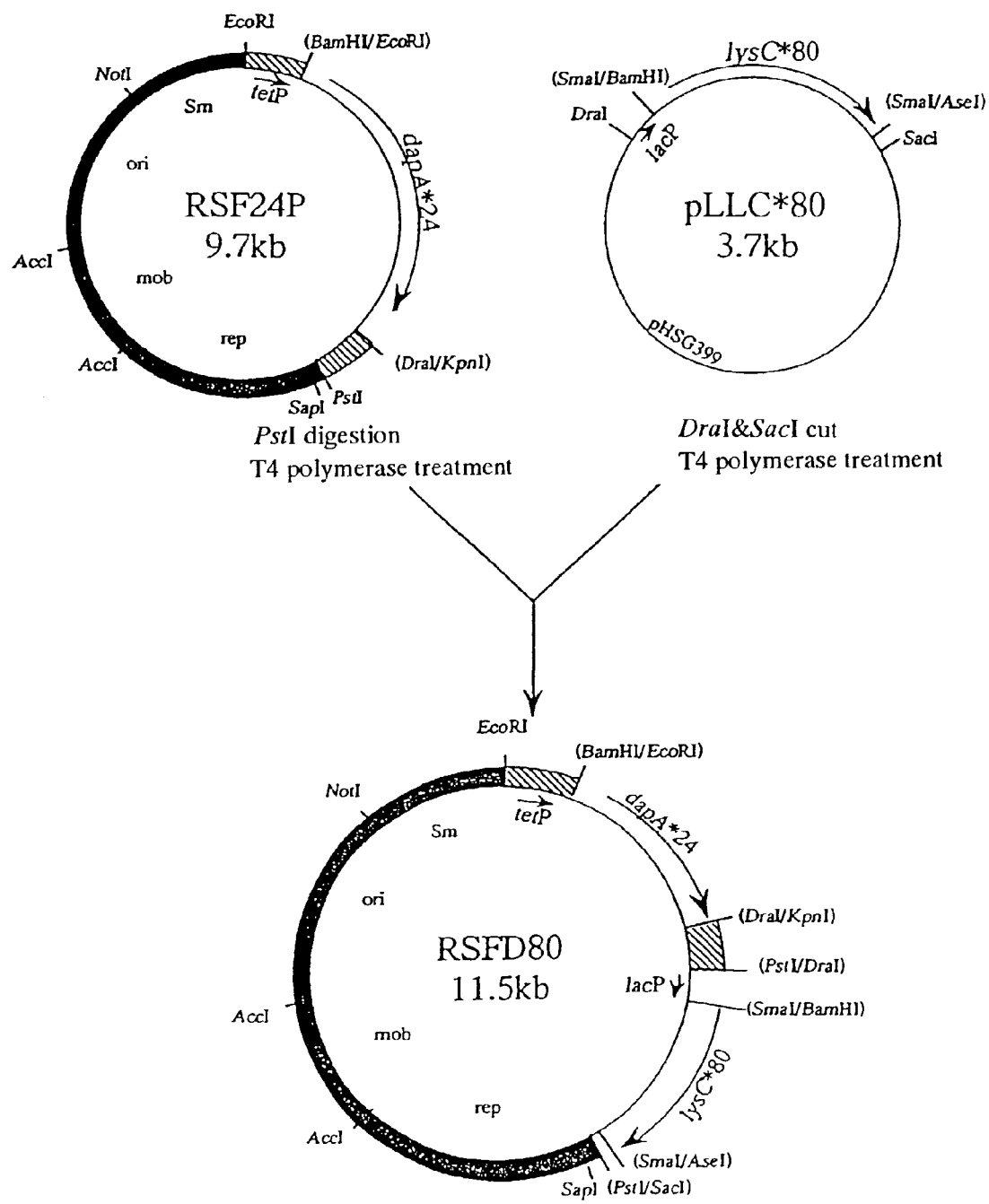
FIG. 2 shows a production process of plasmid RSFD80 containing dapA*24 and lysC*80.

Based on the known lysC nucleotide sequence of *E. coli* (J. Biol. Chem., 261, 1052 (1986)), a fragment containing the SD sequence and ORF of lysC was amplified by PCR. The amplified fragment was ligated to a multi-copy vector pUC18 to obtain a plasmid pLYSC1, in which lysC was ligated so that the transcription direction of lysC was reverse to the transcription direction by the lacZ promoter in pUC18. The plasmid pLYSC1 was subjected to a mutagenesis treatment by using hydroxylamine, and pLYSC1 subjected to the mutagenesis treatment was introduced into *E. coli* GT3. From the transformants, those exhibiting AEC resistance and L-lysine resistance were selected. Further, pLYSC1 was introduced into *E. coli* MC1061, then the cells were subjected to a mutagenesis treatment by using hydroxylamine, and those exhibiting AEC resistance and L-lysine resistance were selected. Further, degree of the inhibition by L-lysine and thermal stability of AK encoded by the plasmids harbored by the selected resistant strains were measured, and a strain which was desensitized to the inhibition by L-lysine and which exhibited superior stability was selected. The plasmid pLYSC1*80, which was confirmed to have change of 352nd C to T by sequencing, was ligated to pHSG399 at a position downstream from the lacZ promoter to obtain pLLC*80. From pLLC*80 and RSF24P, RSFD80 was constructed as shown in FIG. 2.

An *E. coli* JM109 strain into which RSFD80 was introduced was designated as AJ12396, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 28, 1993 and received an accession number of FERM P-13936. Then, it was transferred to an international deposition under the provisions of the Budapest Treaty on Nov. 1, 1994, and received an accession number of FERM BP-4859.

(3) pCAB1

Figure 3:
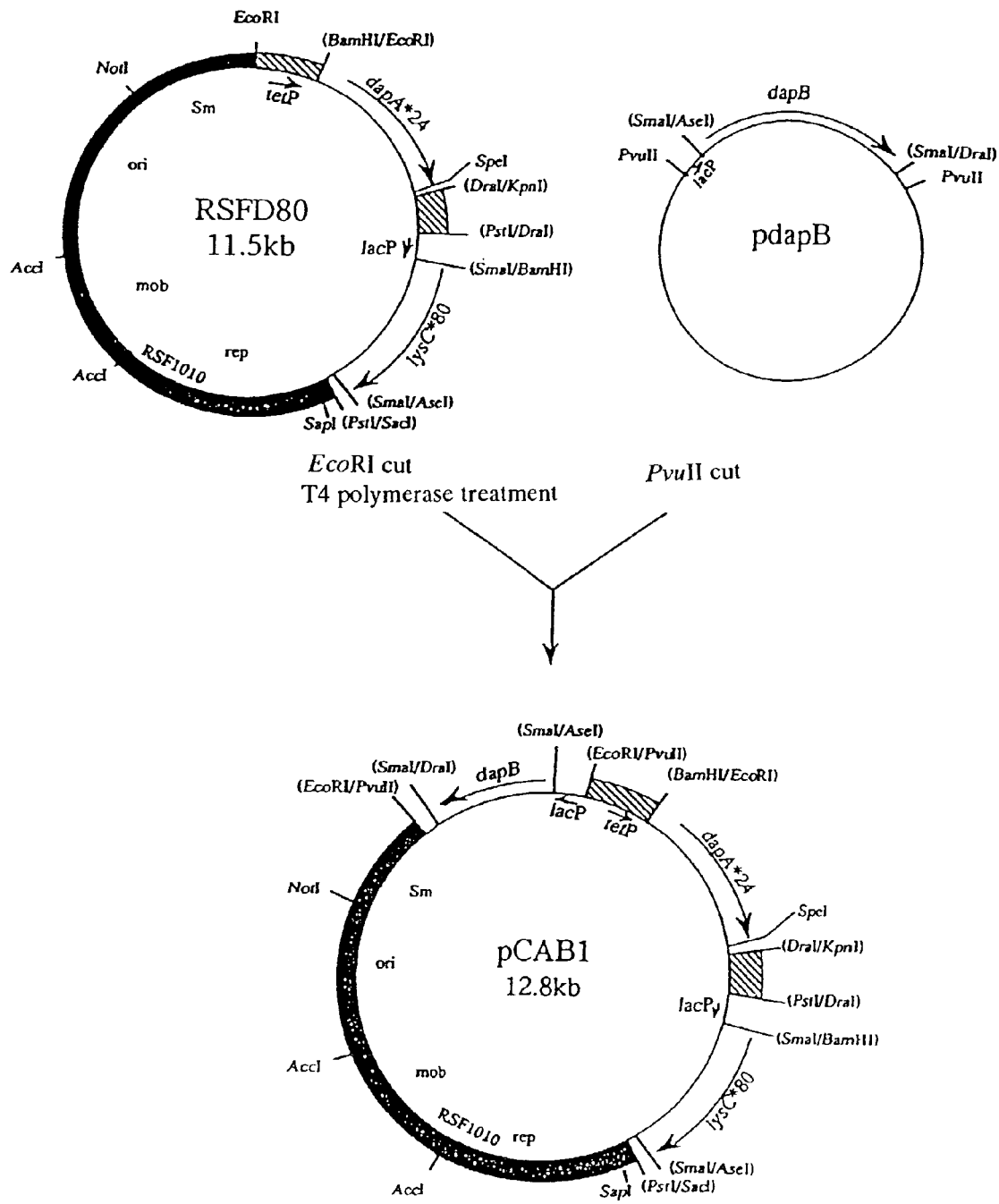
FIG. 3 shows a production process of plasmid pCAB1 containing dapA*24, lysC*80 and dapB.

Based on the known dapB nucleotide sequence (Bouvier, J. et al., J. Biol. Chem., 259, 14829 (1984)), dapB was amplified from *E. coli* W3110 strain chromosome DNA by PCR. The obtained amplified DNA fragment was digested with AseI and DraI, and the obtained fragment was blunt-ended and inserted into the SmaI site of pMW119 to obtain a plasmid pdapB. Subsequently, dapB was introduced into RSFD80 as shown in FIG. 3 to obtain pCAB1.

(4) pCABD2

Figure 4:
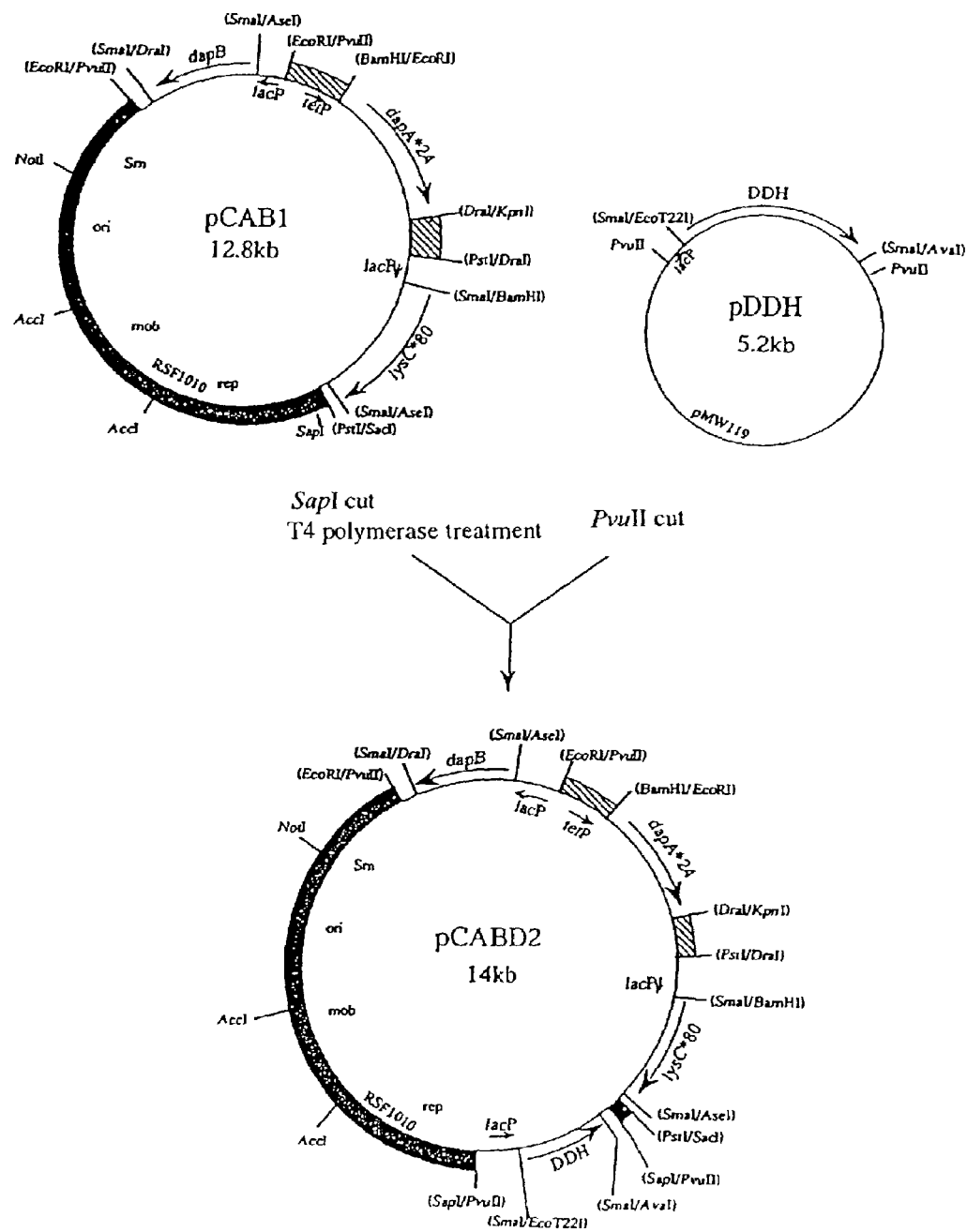
FIG. 4 shows a production process of plasmid pCABD2 containing dapA*24, lysC*80, dapB and ddh.

Based on the known ddh nucleotide sequence of *Corynebacterium glutamicum* (Ishino, S. et al., Nucleic Acids Res., 15, 3917 (1987)), ddh was amplified from chromosome DNA of *Brevibacterium lactofermentum* ATCC13869 by PCR. The obtained amplified DNA fragment was digested with EcoT22I and AvaI, and the obtained fragment was blunt-ended and inserted into the SmaI site of pMW119 to obtain a plasmid pddh. Subsequently, ddh was introduced into pCAB1 as shown in FIG. 4 to obtain a plasmid pCABD2.

(5) pCABDE1

Figure 5:
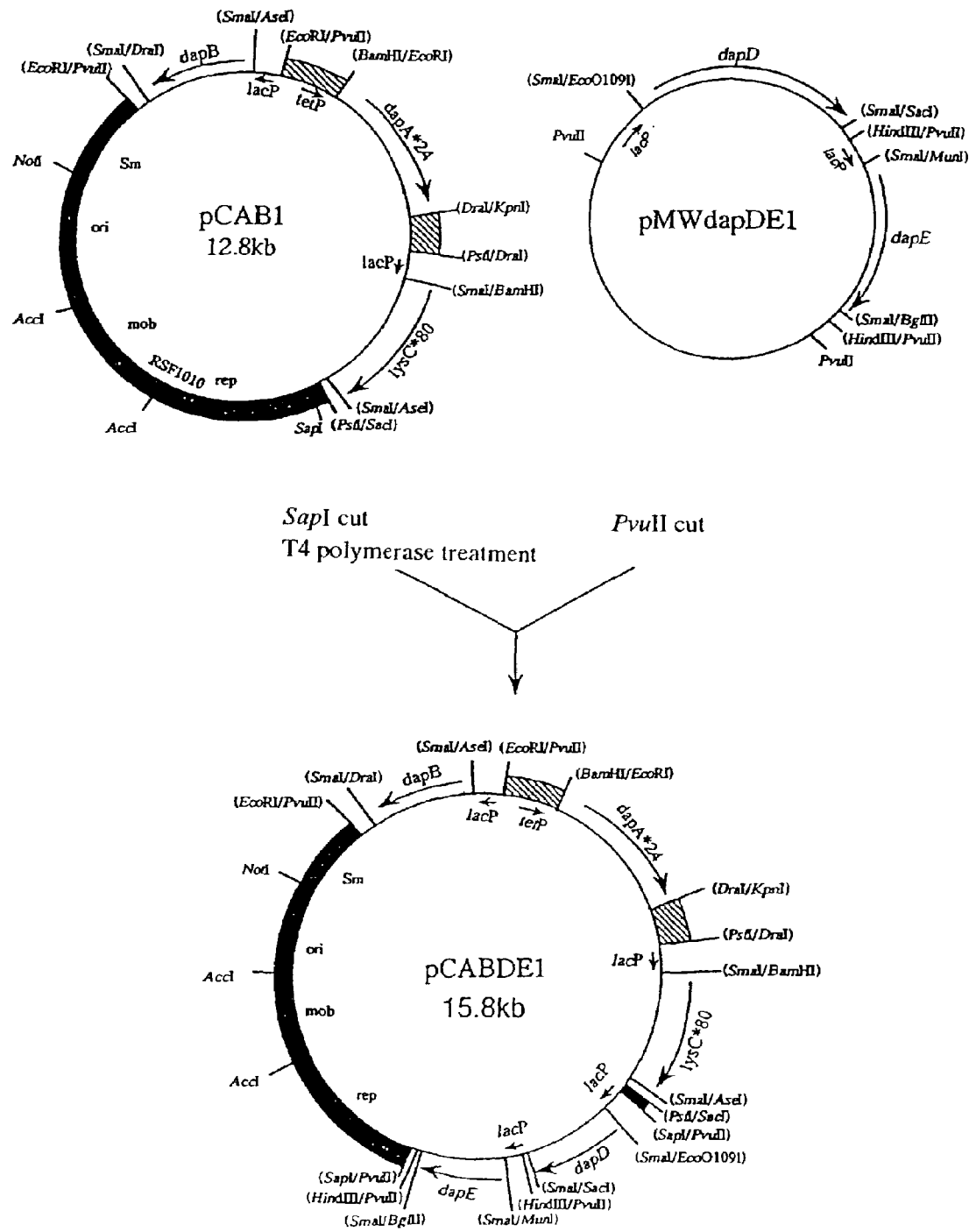
FIG. 5 shows a production process of the plasmid pCABDE1 containing dapA*24, lysC*80, dapB, dapD and dapE.
Figure 6:
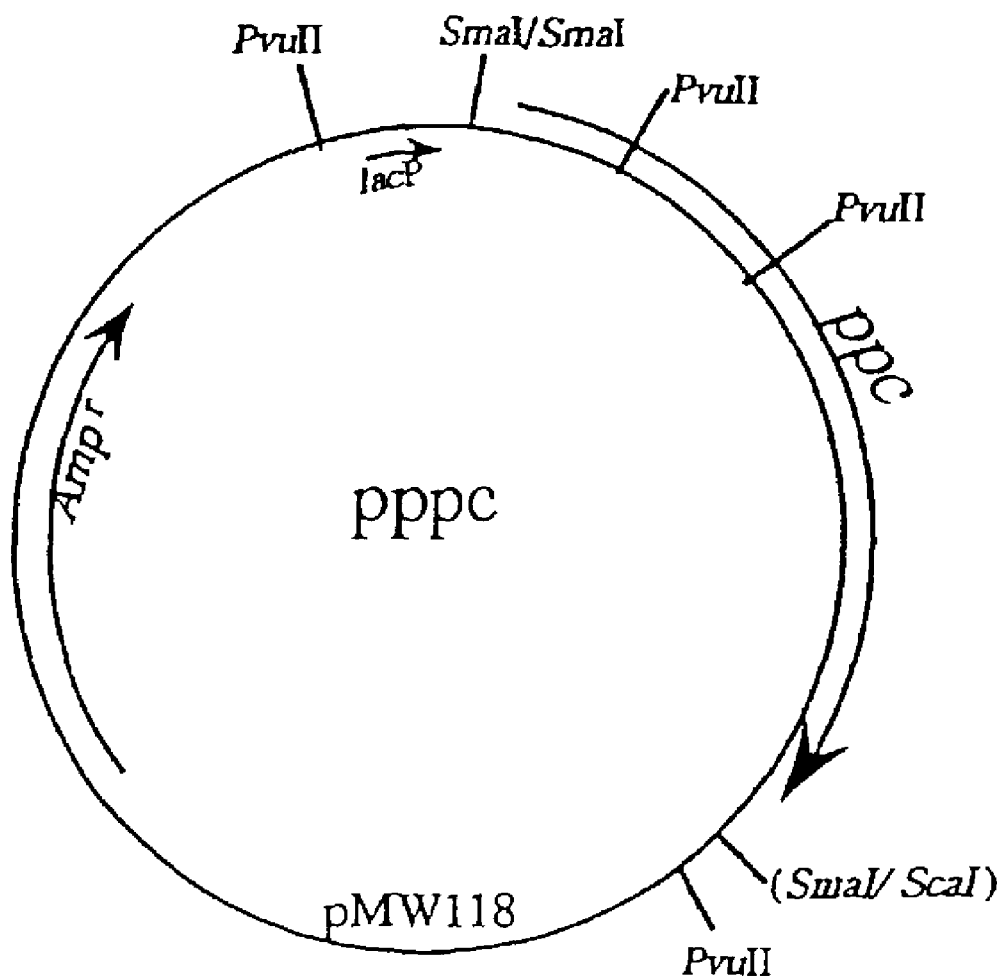
FIG. 6 shows structure of plasmid pppc containing ppc.
Figure 7:
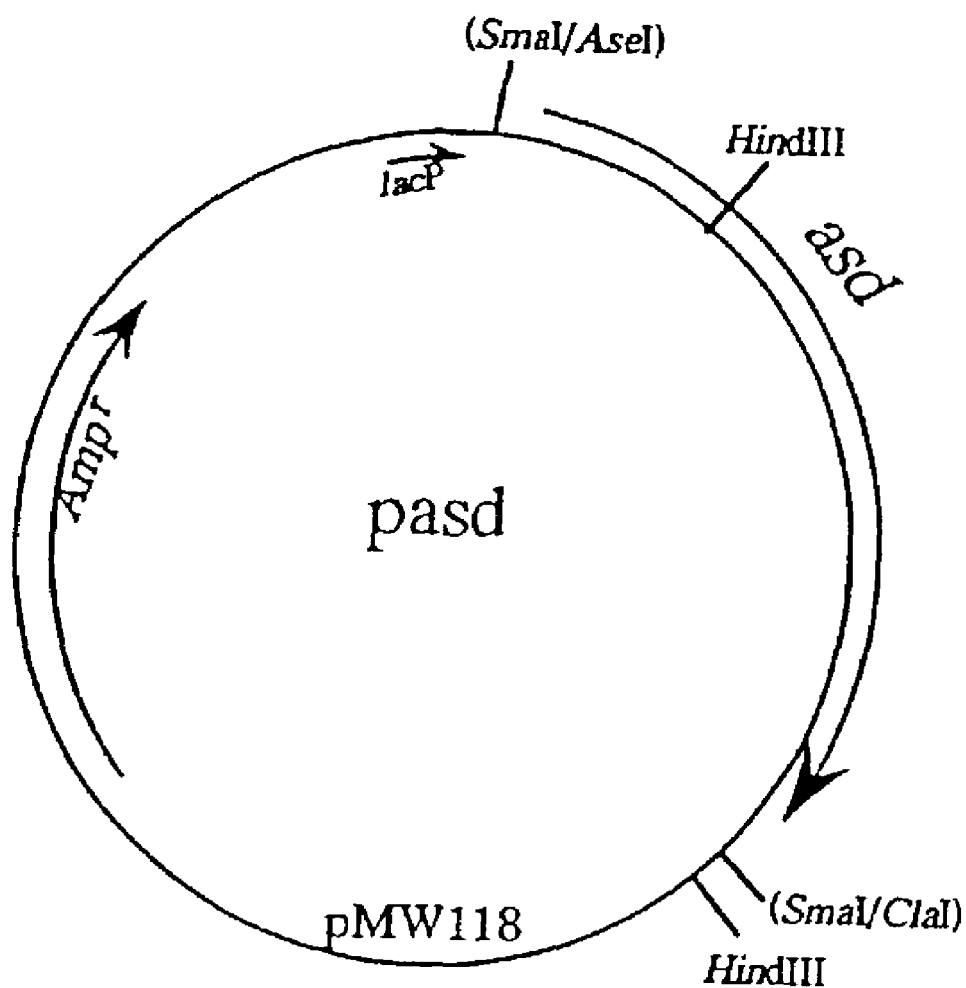
FIG. 7 shows structure of plasmid pasd containing asd.

Based on the known dapD nucleotide sequence (Richaud, C. et al., J. Biol. Chem., 259, 14824 (1984)), dapD was amplified from chromosome DNA of *E. coli* W3110 strain by PCR. The obtained amplified DNA fragment was digested with EcoO109I and SacI, and the obtained fragment was blunt-ended and inserted into the SmaI site of pMW118 to obtain a plasmid pdapD. Further, based on the known dapE nucleotide sequence (Bouvier, J. et al., J. Bacteriol., 174, 5265 (1992)), dapE was amplified from chromosome DNA of *E. coli* W3110 strain by PCR. The obtained amplified DNA fragment was digested with MunI and BglII, and an obtained fragment was blunt-ended and inserted into the SmaI site of pMW118 to obtain a plasmid pdapE. Further, dapE was excised from pdapE and inserted into pdapD to obtain a plasmid pMWdapDE1 containing both of dapE and dapD. As shown in FIG. 5, a fragment containing dapE and dapD was excised from pMWdapDE1, and inserted into pCAB1 to obtain pCABDE1.

A plasmid pCABD(B) was constructed as follows.

First, a DNA fragment containing the promoter site of Tet resistance gene was amplified from pBR322 by using primers having the following sequences. 5'-TCAAGAATTCTCATGTTTGA-3' (SEQ ID NO: 1) 5'-GTTAGATTTGGTACCCGGTGCCTGACTGCGTTAGC-3' (SEQ ID NO: 2)

Figure 18:
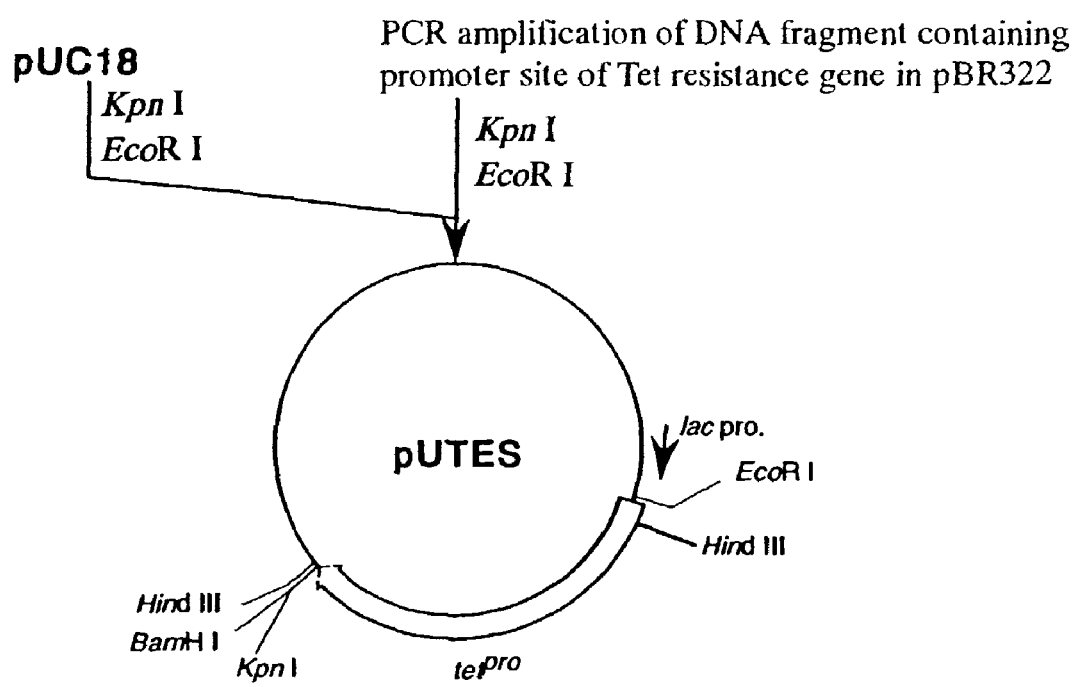
FIG. 18 shows a production process of plasmid pUTES containing $tet^{pro}$.

The amplified DNA fragment was digested with KpnI and EcoRI, and inserted between KpnI and EcoRI cleavage sites of pUC18 to obtain pUTES (FIG. 18).

Then, the Brev. dapA gene was amplified by using primers having the following sequences and chromosome DNA of *Brevibacterium lactofermentum* Ysr strain as a template. 5'-GGTTGTGGTACCCCCAAATGAGGGAAGAAG-3' (SEQ ID NO: 3) 5'-TGGAACCTCTGTTGCTGCAG-3' (SEQ ID NO: 4)

Figure 19:
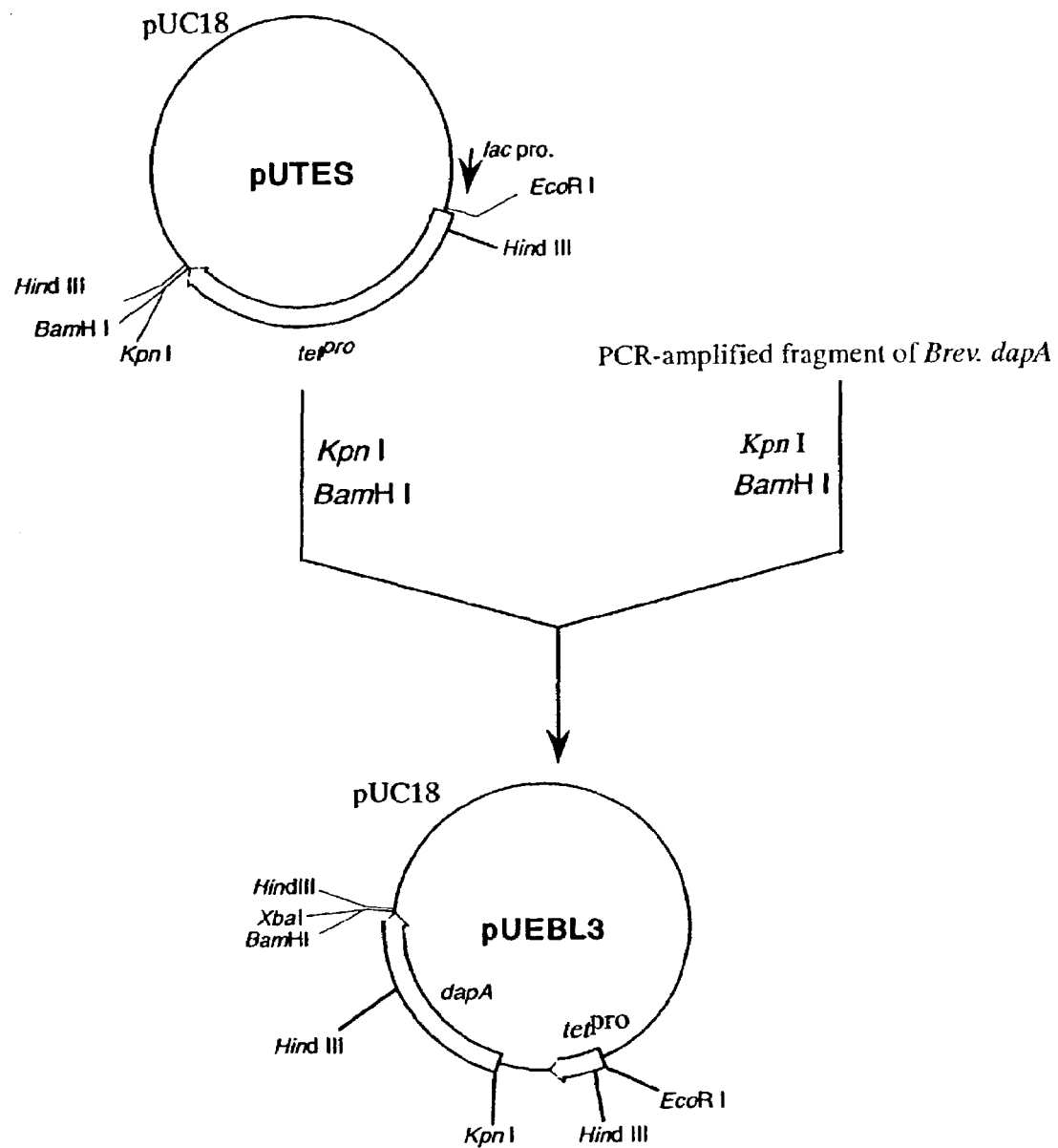
FIG. 19 shows a production process of plasmid pUEBL3, containing $tet^{pro}$ and dapA derived from *Brevibacterium lactofermentum* downstream from $tet^{pro}$.

The amplified Brev. dapA gene was digested with KpnI and BamHI, and inserted between KpnI and BamHI cleavage sites of pUTES to obtain pUEBL3 (FIG. 19).

Figure 20:
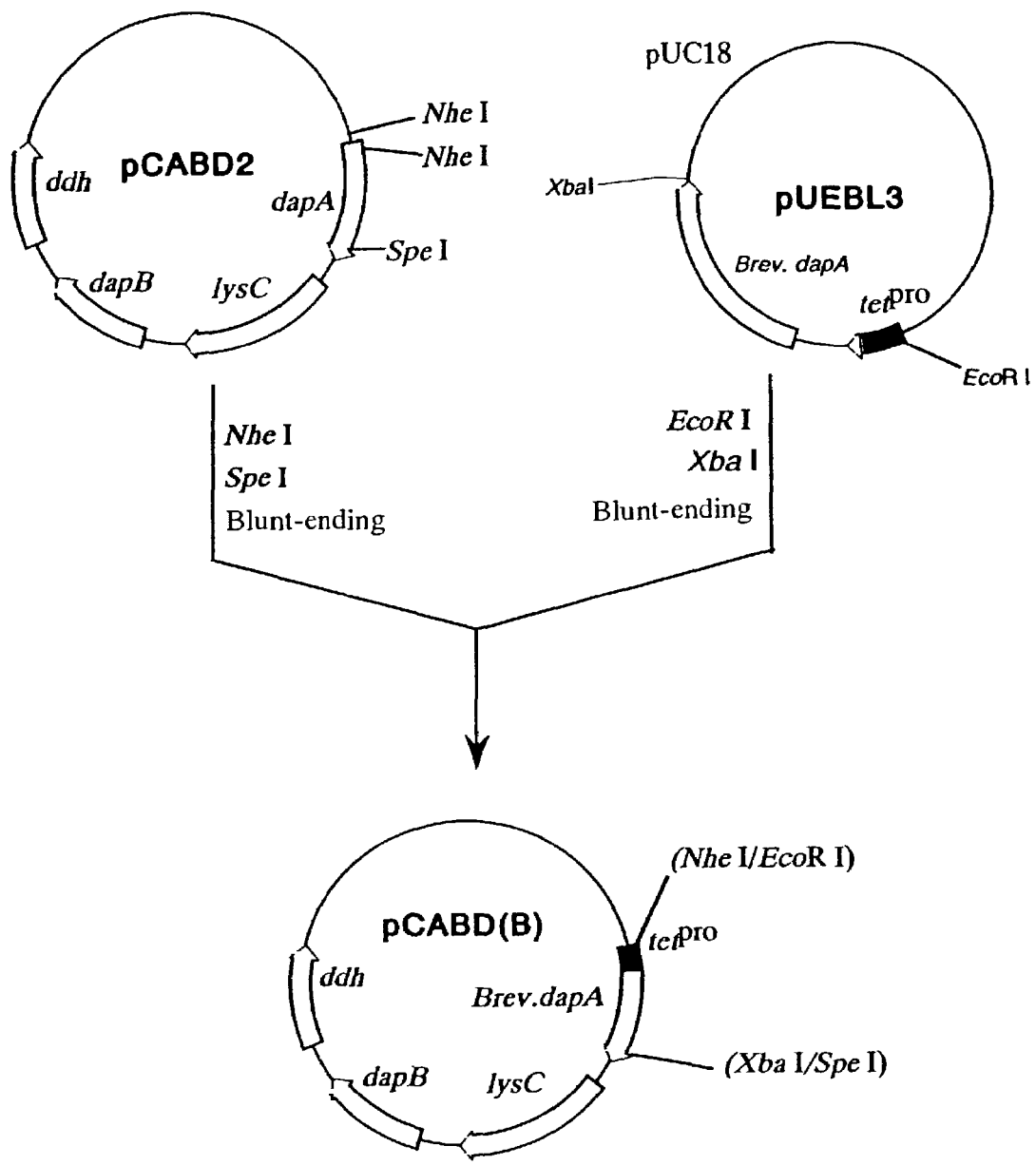
FIG. 20 shows a production process of plasmid pCABD(B) containing dapA derived from *Brevibacterium lactofermentum* (Brev. dapA), lysC, dapB and ddh.

Then, pUEBL3 was digested with EcoRI and XbaI, and blunt-ended for the both ends to obtain a fragment containing Brev. dapA. Thereafter, pCABD2 mentioned in International Publication No. WO95/16042 was digested with NheI and SpeI and blunt-ended for the both ends. A fragment containing lysC, dapB and ddh was collected, and then the previously obtained fragment containing Brev. dapA was inserted thereto to obtain pCABD(B) (FIG. 20)

While *E. coli* W3110 (tyrA) is detailed in European Patent Publication No. 488424, the preparation method therefor will be briefly explained below. The *E. coli* W3110 strain was obtained from the National Institute of Genetics (Shizuoka-ken, Mishima-shi). This strain was inoculated on an LB plate containing streptomycin, and a strain that formed a colony was selected to obtain a streptomycin resistant strain. The selected streptomycin resistant strain and *E. coli* K-12 ME8424 strain were mixed and cultured in a complete medium (L-Broth: 1% Bacto trypton, 0.5% Yeast extract, 0.5% NaCl) as stationary culture at 37° C. for 15 minutes to induce conjugation. The *E. coli* K-12 ME8424 strain has genetic traits of HfrPO45, thi, relA1, tyrA::Tn10, ung-1 and nadB, and can be obtained from the National Institute of Genetics.

Then, the culture was inoculated to a complete medium (L-Broth: 1% Bacto trypton, 0.5% yeast extract, 0.5% NaCl, 1.5% agar) containing streptomycin, tetracycline and L-tyrosine, and a strain that formed a colony was selected. This strain was designated as *E. coli* W3110 (tyrA) strain.

Many strains formed by introducing a plasmid into the W3110 (tyrA) strain are disclosed in European Patent Publication No. 488424. For example, a strain obtained by introducing a plasmid pHATerm was designated as *E. coli* W3110 (tyrA)/pHATerm strain (*E. coli* AJ12662 strain), and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Nov. 16, 1991 as an international deposition and received an accession number of FERM BP-3653. The W3110 (tyrA) strain can also be obtained by eliminating the plasmid pHATerm from this *E. coli* W3110 (tyrA)/pHATerm strain. The elimination of the plasmid can be performed in a conventional manner.

<2> Introduction of Aspartate-Semialdehyde Dehydrogenase Gene (asd), Phosphoenolpyruvate Carboxylate Gene (ppc) or Aspartase Gene (aspA), and Evaluation of L-Lysine Productivity As a plasmid containing asd and a plasmid containing ppc, pasd and pppc described in International Publication No. WO95/16042 were used. Constructions of these plasmids were detailed in International Publication No. WO95/16042. The outlines are as follows.

(1) pasd

Figure 8:
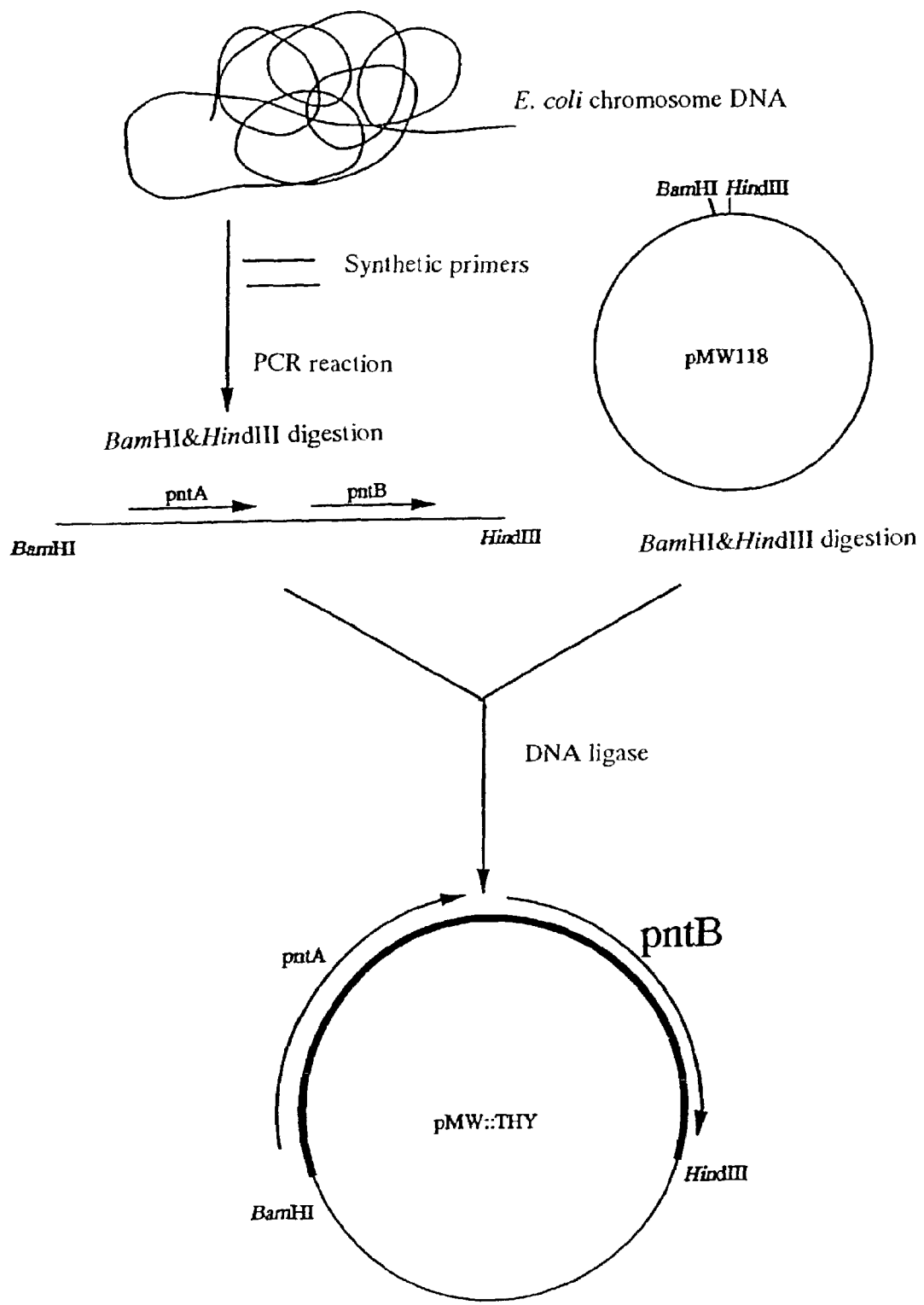
FIG. 8 shows a production process of plasmid pMW::THY containing pntAB (pntA and pntB).

The plasmid asd was obtained from a plasmid pAD20 (Haziza, C. et al., EMBO, 1, 379 (1982)), which contained the gene. The plasmid pAD20 was digested with AseI and ClaI, blunt-ended and inserted into the SmaI site of pMW118 to obtain a plasmid pasd (FIG. 8).

(2) pppc

Figure 9:
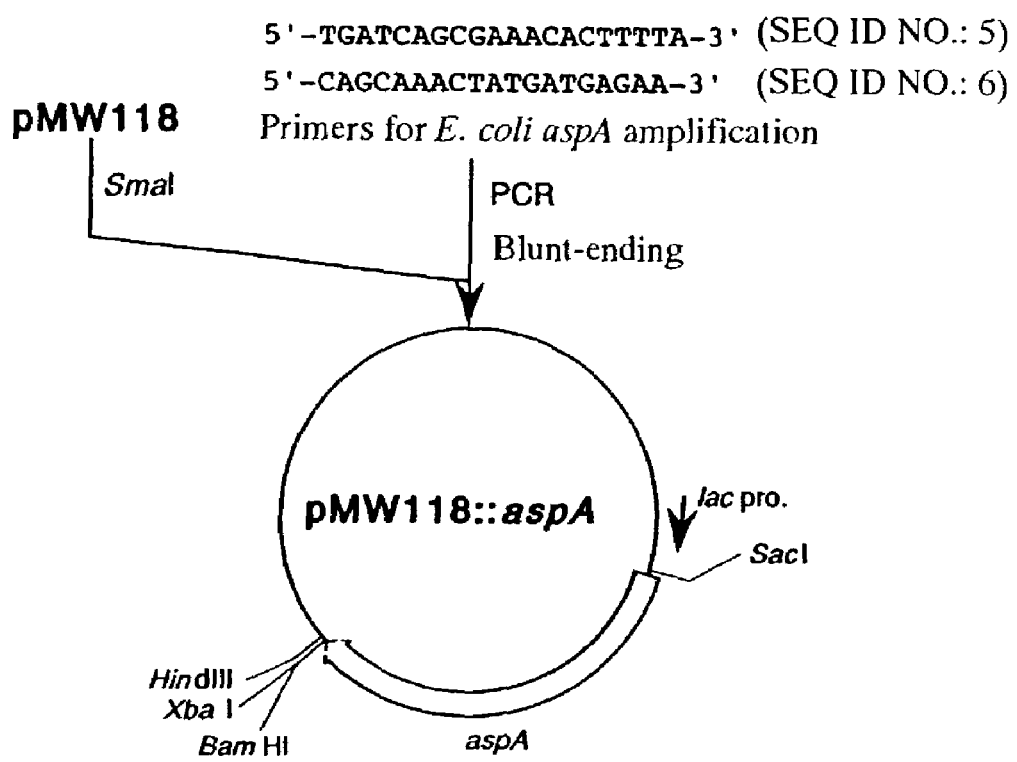
FIG. 9 shows a production process of plasmid pMW118::aspA containing aspA.

The plasmid pppc was obtained from a plasmid pT2 that contained the gene. The plasmid pT2 was digested with SmaI and ScaI, blunt-ended, and inserted into the SmaI site of pMW118 to obtain a plasmid pppc (FIG. 9). An *E. coli* F15 strain (AJ12873) harboring pT2 was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Jul. 15, 1993 and received an accession number of FERM P-13752. Then, it was transferred to an international deposition under the provisions of the Budapest Treaty on Jul. 11, 1994, and received an accession number of FERM BP-4732.

A plasmid containing aspA was constructed as follows.

The aspA gene of *E. coli* was amplified by using primers having the following sequences. 5'-TGATCAGCGAAACACTTTTA-3' (SEQ ID NO: 5) 5'-CAGCAAACTATGATGAGAA-3' (SEQ ID NO: 6)

Then, the obtained amplified fragment was inserted into the SmaI cleavage site of pMW118 (Nippon Gene) to obtain pMW118::aspA (FIG. 9).

Each of pMW118 (control plasmid), pasd, pppc and pMW118::aspA (comparative plasmid) was introduced into each of *E. coli* W3110 (tyrA) and the transformants obtained in the aforementioned <1>. The obtained transformants, except for those obtained by introducing pMW118, pasd, pppc or pMW118::aspA into *E. coli* W3110 (tyrA), contained two kinds of plasmids, i.e. one of pMW118, pasd, pppc and pMW118::aspA and one of RSF24P, RSFD80, pCAB1, pCABD2, pCABD(B) and pCABDE1. These transformants were examined for L-lysine productivity by the method described in International Publication No. WO95/16042. The specific procedure was as follows.

The cells were cultured in 20 ml of a medium having the following composition contained in a 500-ml Sakaguchi flask at a temperature of 37° C. for 30 hours with stirring at 114-116 rpm.

(Medium Composition)
Glucose 40 g/l
$MgSO_4.7H_2O$ 1 g/l
$(NH_4)_2SO_4$ 16 g/l
$KH_2PO_4$ 1 g/l
$FeSO_4.7H_2O$ 0.01 g/l
$MnSO_4.5H_2O$ 0.01 g/l
Yeast Extract (Difco) 2 g/l
L-Tyrosine 0.1 g/l
Adjusted to pH 7.0 with KOH, and autoclaved at 115° C. for 10 minute (glucose and $MgSO_4.7H_2O$ were separately sterilized).
$CaCO_3$ 25 g/l
(according to the Pharmacopoea of Japan, sterilized by dry heat at 180° C. for 2 days)
Antibiotic (20 mg/l of streptomycin, 50 mg/l of ampicillin or 25 mg/l of kanamycin depending on the kind of the plasmid to be introduced)

L-Lysine in the culture broth (medium after the culture) was quantified by using Biotech Analyzer AS210 produced by Asahi Chemical Industry Co., Ltd.

The results are shown in Table 1. In the table, the amount of L-lysine is indicated in terms of mg per dl of the medium.

TABLE 1

| | Lys accumulation (mg/dl) | | | |
|---|---|---|---|---|
| | pMW118 | pasd | pppc | pMW118::aspA |
| — | 40 | 50 | 60 | 60 |
| RSF24P | 350 | 340 | 360 | 350 |
| RSFD80 | 960 | 790 | 990 | 960 |
| pCAB1 | 1120 | 1140 | 1150 | 1130 |
| PCABD2 | 1230 | 1320 | 1380 | 1240 |
| pCABD(B) | 1230 | 1320 | 1370 | n.d. |
| PCABDE1 | 1210 | 1310 | 1350 | n.d. | n.d.: Not determined

As clearly seen from the results shown in Table 1, when asd or ppc was enhanced each alone or together with dapA (RSF24P), dapA+lysC (RSFD80) or dapA+lysC+dapB (pCAB1) in *E. coli*, the production amount of L-lysine (accumulated amount) was not changed or only slightly changed and, as for asd, it might be reduced compared with the case where asd or ppc was not enhanced (−180 to 20 mg/dl as for asd, 10 to 30 mg/dl as for ppc). In contrast, if they were enhanced together with dapA+lysC+dapB+ddh (pCABD2) or dapA+lysC+dapB+dapD+dapE (pCABDE1), marked increase of the L-lysine production amount was observed compared with the case where asd or ppc was not enhanced (70 mg/dl as for asd, 90 mg/dl as for ppc). However, when aspA was enhanced with dapA+lysC+dapB+ddh (pCABD2), marked increase of the L-lysine production amount was not observed. Furthermore, even when dapA derived from *Brevibacterium lactofermentum* was used instead of dapA derived from *Escherichia coli* (pCABD (B)), the same effect was obtained as the case where dapA derived from *Escherichia coli* was used (pCABD2). Therefore, the origin of the genes is not considered important, but the combination thereof is important.

Example 2

<1> Construction of Plasmids Containing Phosphoenolpyruvate Carboxylase Gene (ppc) and Aspartate-Semialdehyde Dehydrogenase Gene (asd), Transhydrogenase Gene (pntAB) or Aspartase Gene (aspA)

A plasmid containing ppc and asd, a plasmid containing ppc and pntAB, and a plasmid containing ppc and aspA were constructed as follows.

(1) Plasmid Containing ppc and asd (ppcd)

Figure 10:
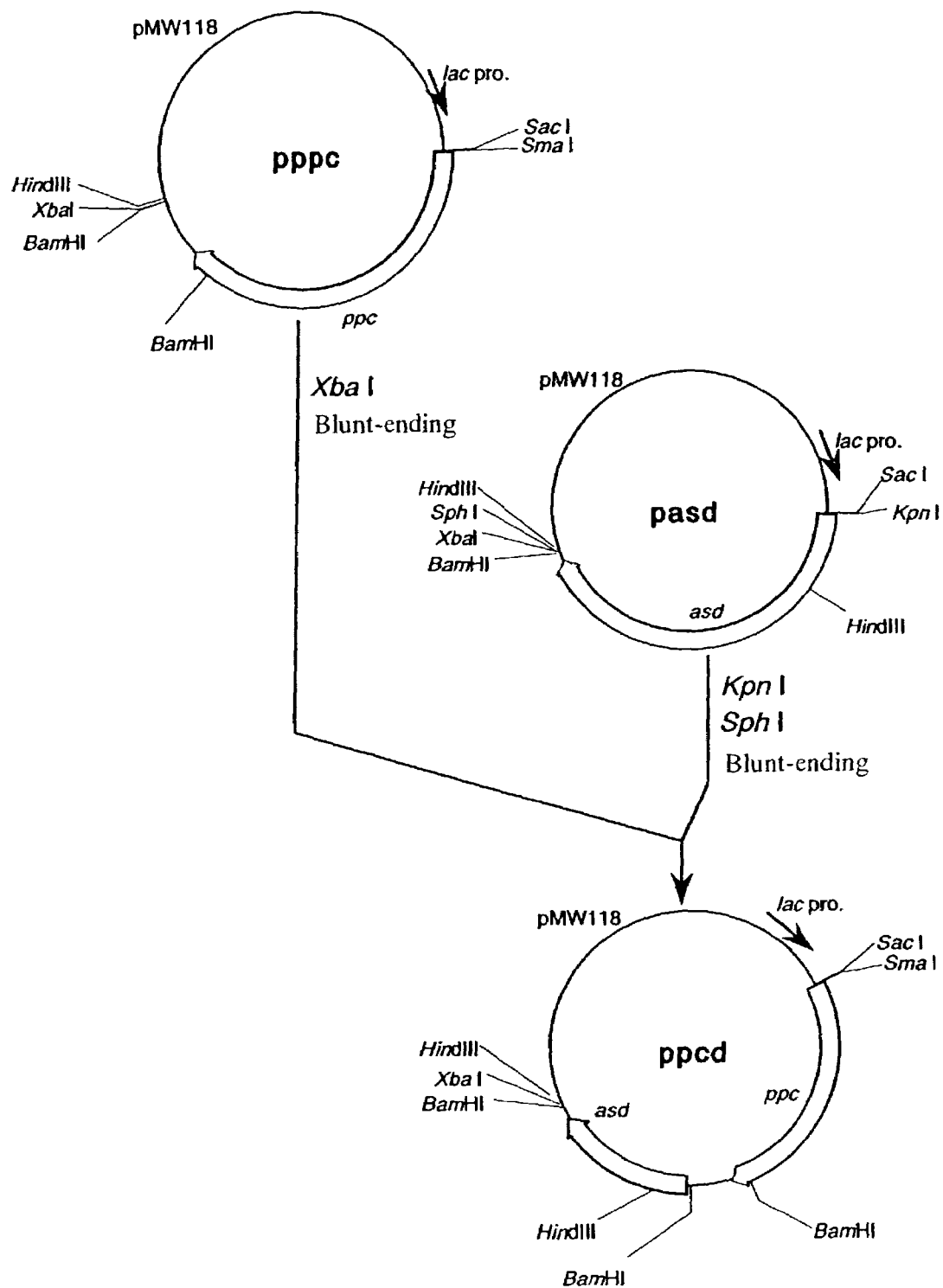
FIG. 10 shows a production process of plasmid ppcd containing ppc and asd.

The plasmid pasd disclosed in International Publication No. WO95/16042 was digested with KpnI and SphI, and the DNA fragment containing asd was blunt-ended for the both ends. Then, pppc disclosed in International Publication No. WO95/16042 was digested with XbaI and blunt-ended for the both ends, and the previously obtained asd fragment was inserted thereto to obtain ppcd (FIG. 10).

(2) Plasmid Containing ppc and pntAB (pPTS)

Figure 11:
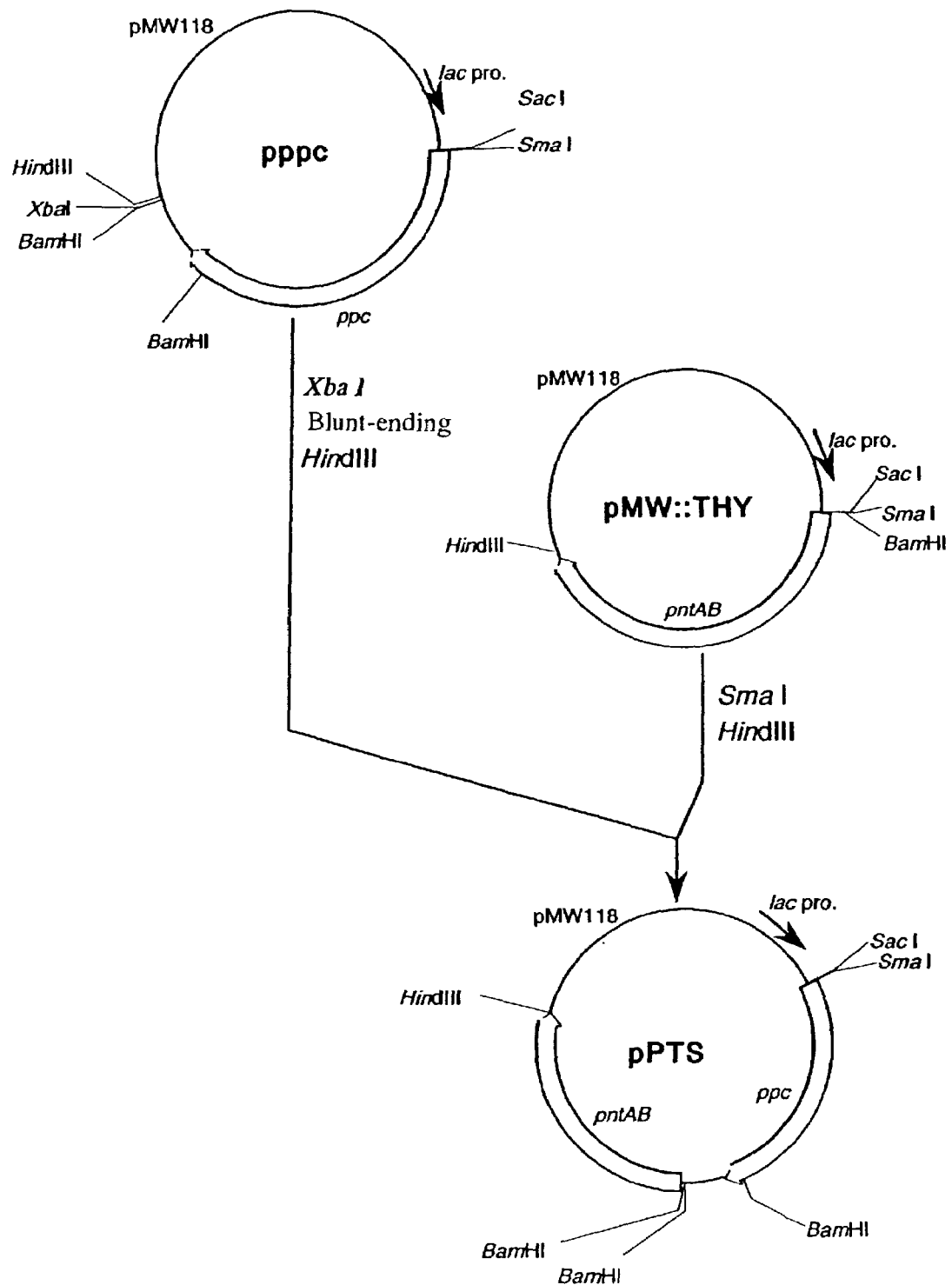
FIG. 11 shows a production process of plasmid pPTS containing ppc and pntAB.

The plasmid pMW::THY disclosed in International Publication No. WO95/11985 was digested with SmaI and HindIII, and the DNA fragment containing pntAB was collected. Then, pppc disclosed in International Publication No. WO95/16042 was digested with XbaI, blunt-ended for the both ends and further digested with HindIII, and the previously obtained pntAB fragment was inserted at the cleaved site to obtain pPTS (FIG. 11).

Construction of the plasmid pMW::THY is detailed in International Publication No. WO95/11985. It will be outlined below.

Based on the known pntA and pntB nucleotide sequences of *E. coli* (D. M. Clarke et al., Eur. J. Biochem., 158, 647-653 (1986)), a fragment containing the both genes including regions having promoter activity was amplified by PCR. The amplified DNA fragment was digested with BamHI and HindIII, and the obtained DNA fragment was ligated to the plasmid vector pMW118 (Nippon Gene) digested with BamHI and HindIII to obtain pMW::THY (FIG. 8).

The *E. coli* JM109 strain into which pMW118::THY was introduced was designated as AJ12929, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 4, 1993, and received an accession number of FERM P-13890. Then, it was transferred to an international deposition under the provisions of the Budapest Treaty on Sep. 14, 1994, and received an accession number of FERM BP-4798.

(3) Plasmid Containing ppc and aspA (pAPW)

Figure 12:
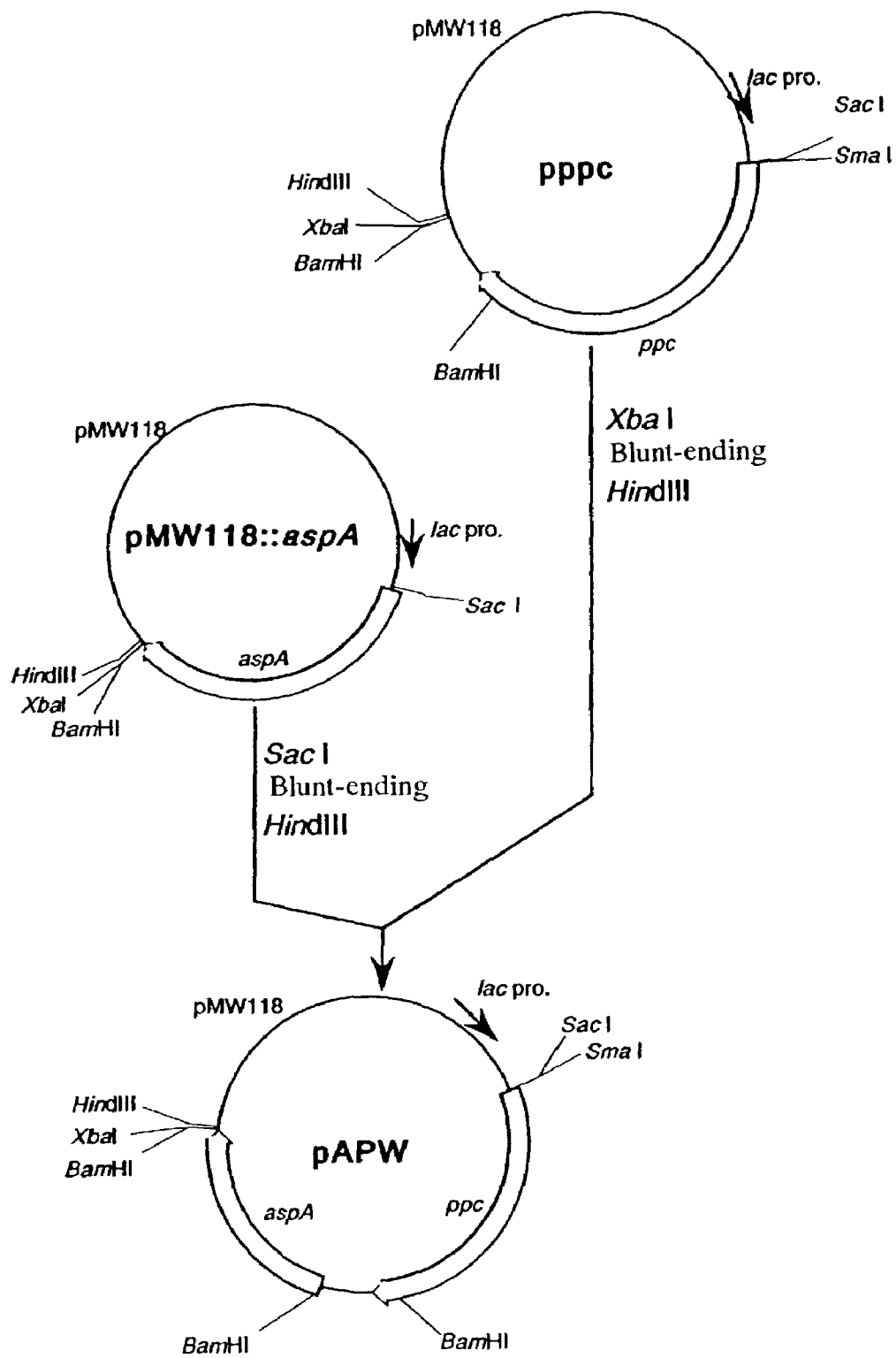
FIG. 12 shows a production process of plasmid pAPW containing ppc and aspA.

The plasmid pMW118::aspA described in the aforementioned Example 1 was digested with SacI, blunt-ended for the both ends, and further digested with HindIII to obtain a DNA fragment containing aspA. Then, pppc described in International Publication No. WO95/16042 was digested with XbaI, blunt-ended for the both ends, and further digested with HindIII, and the previously obtained aspA fragment was inserted into the HindIII cleavage site to obtain pAPW (FIG. 12).

<2> Introduction of Two Kinds of Genes and Evaluation of L-Lysine Productivity To a pCABD2-introduced transformant which was obtained in the aforementioned Example 1, each of pppc (reference plasmid), ppcd, pPTS and pAPW (comparative plasmid) was introduced. The obtained transformants contained two kinds of plasmids, i.e. one of pppc, ppcd, pPTS and pAPW, and pCABD2. These transformants were examined for the L-lysine productivity in the same manner as in Example 1 <2>.

The results are shown in Table 2.

TABLE 2

|  | Lys accumulation (mg/dl) |
| --- | --- |
| pCABD2 + pppc | 1380 |
| pCABD2 + ppcd | 1460 |
| pCABD2 + pPTS | 1450 |
| pCABD2 + pAPW | 1390 |

As clearly seen from the results shown in Table 2, when asd or pntAB was enhanced together with dapA+lysC+dapB+ddh+ppc (ppcd or pPTS), marked increase of the L-lysine production amount was observed (80 mg/dl as for asd, 70 mg/dl as for pntAB). As for aspA, however, even when aspA was enhanced together with dapA+lysC+dapB+ddh+ppc (pAPW), marked increase of the L-lysine production amount was not observed.

Example 3

<1> Construction of Plasmids Containing Phosphoenolpyruvate Carboxylase Gene (ppc), Transhydrogenase Gene (pntAB) and Aspartate-Semialdehyde Dehydrogenase Gene (asd) or Aspartase Gene (aspA)

A plasmid containing ppc, pntAB and asd genes and a plasmid containing ppc, pntAB and aspA were constructed as follows.

(1) Plasmid Containing ppc, pntAB and asd (pPTd)

Figure 13:
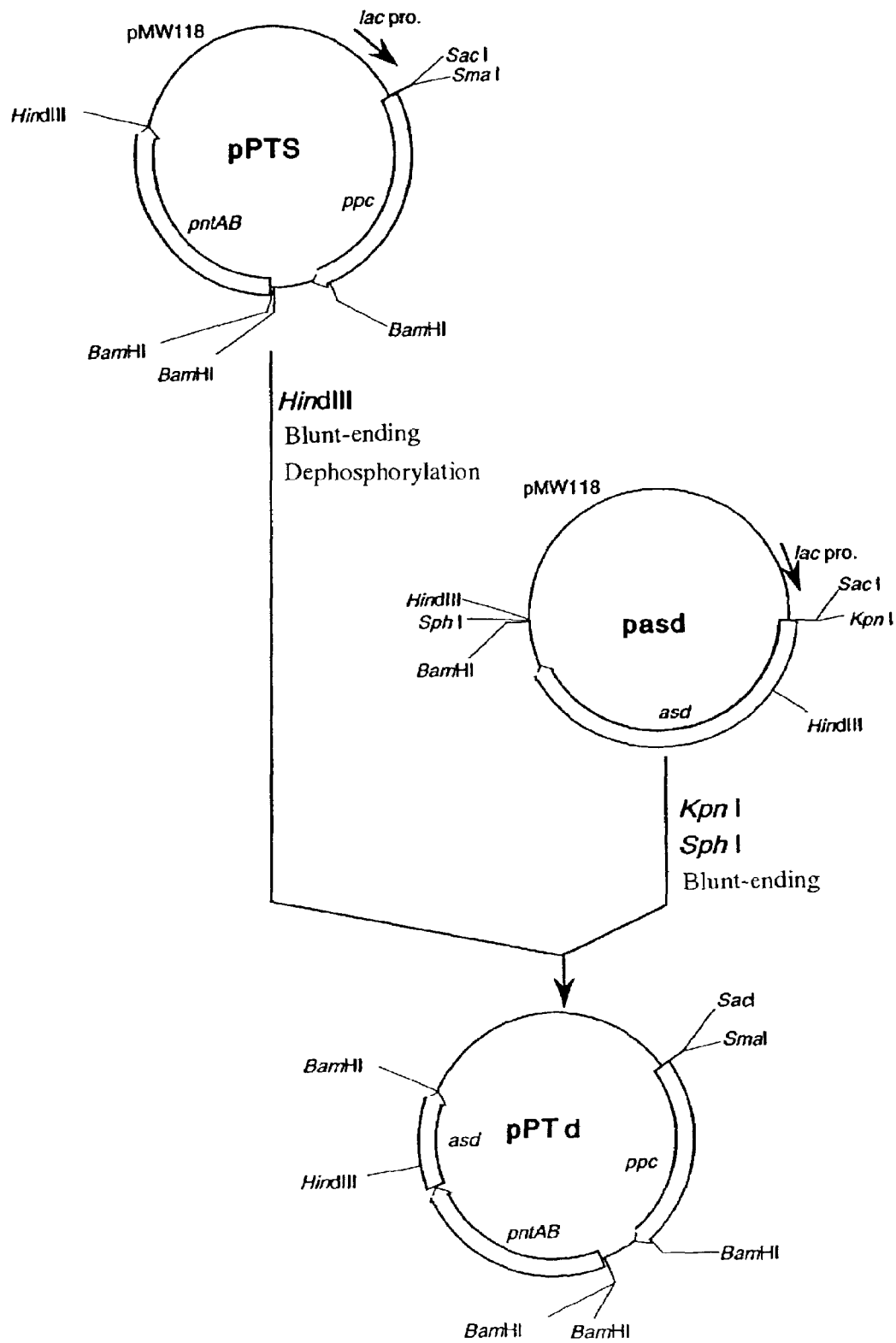
FIG. 13 shows a production process of plasmid pPTd containing ppc, pntAB and asd.

The plasmid pasd described in International Publication No. WO95/16042 was digested with KpnI and SphI, and the DNA fragment containing asd was blunt-ended for the both ends. Then, pPTS described in the aforementioned Example 2 was digested with HindIII and blunt-ended, and the previously obtained asd fragment was inserted into the HindIII cleavage site to obtain pPTd (FIG. 13).

(2) Plasmid Containing ppc, pntAB and aspA (pAPT)

Figure 14:
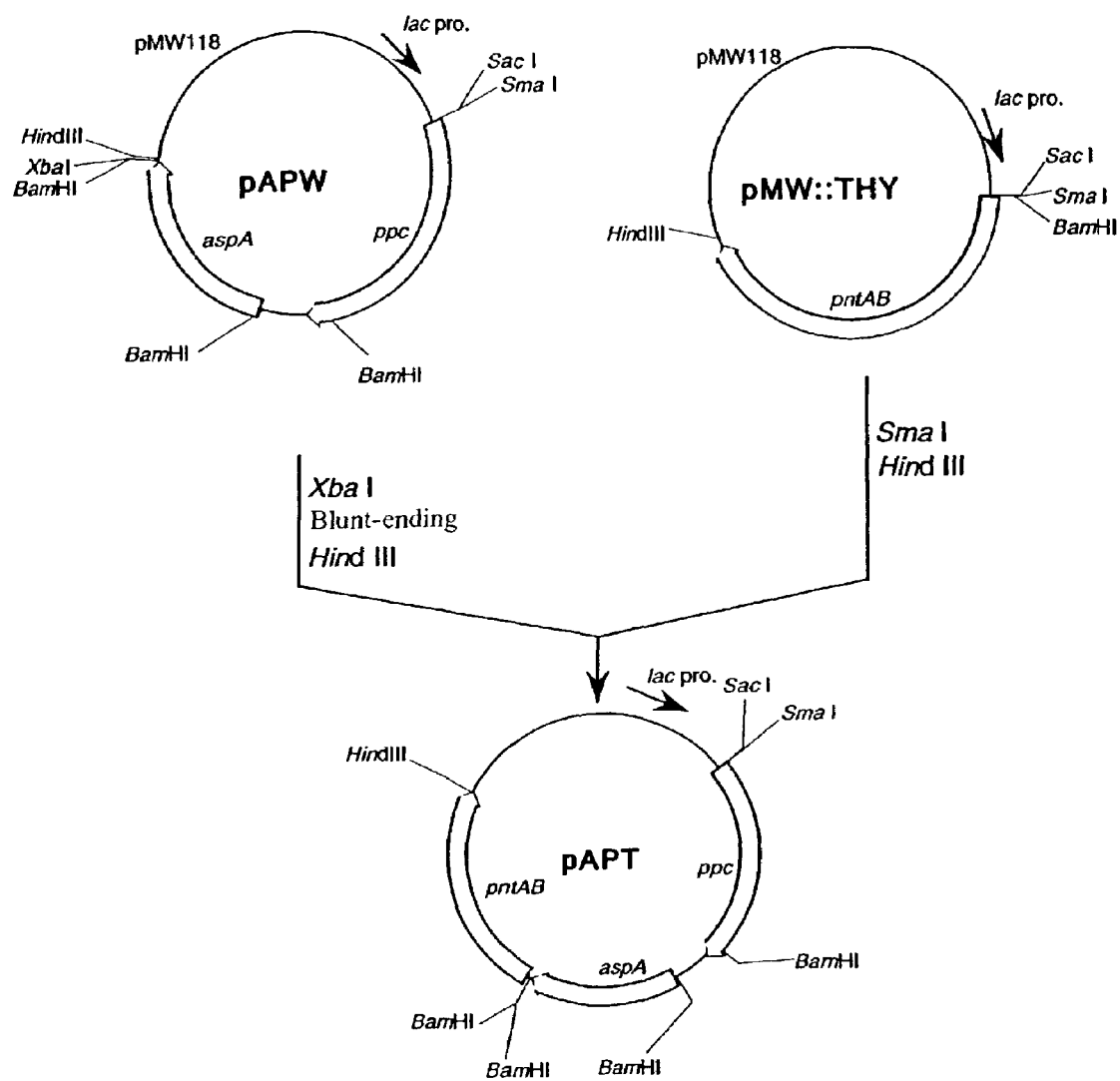
FIG. 14 shows a production process of plasmid pAPT containing ppc, pntAB and aspA.

The plasmid pMW::THY described in International Publication No. WO95/11985 was digested with SmaI and HindIII to obtain a DNA fragment containing pntAB. Then, pAPW described in the aforementioned Example 2 was digested with XbaI, blunt-ended for the both ends, and further digested with HindIII. The previously obtained fragment containing pntAB was inserted into the HindIII cleavage site to obtain pAPT (FIG. 14).

<2> Introduction of Three Kinds of Genes and Evaluation of L-Lysine Productivity To a pCABD2-introduced transformant which was obtained in the aforementioned Example 1, pPTS (reference plasmid), pPTd or pAPT was introduced. The obtained transformants contained two kinds of plasmids, i.e. one of pPTS, pPTd and pAPT, and pCABD2. These transformants were examined for the L-lysine productivity in the same manner as in Example 1 <2>.

The results are shown in Table 3.

TABLE 3

|  | Lys accumulation (mg/dl) |
| --- | --- |
| pCABD2 + pPTS | 1450 |
| pCABD2 + pPTd | 1510 |
| pCABD2 + pAPT | 1500 |

As clearly seen from the results shown in Table 3, when asd or aspA was enhanced together with dapA+lysC+dapB+ddh+ppc+pntAB (pPTd or pAPT), marked increase of the L-lysine production amount was observed (60 mg/dl as for asd, 50 mg/dl as for aspA).

Example 4

<1> Construction of Plasmids Containing Phosphoenolpyruvate Carboxylase Gene (ppc), Transhydrogenase Gene (pntAB), Aspartate-Semialdehyde Dehydrogenase Gene (asd) and Aspartase (aspA) Gene A plasmid containing ppc, pntAB, asd and aspA was constructed as follows.

Figure 15:
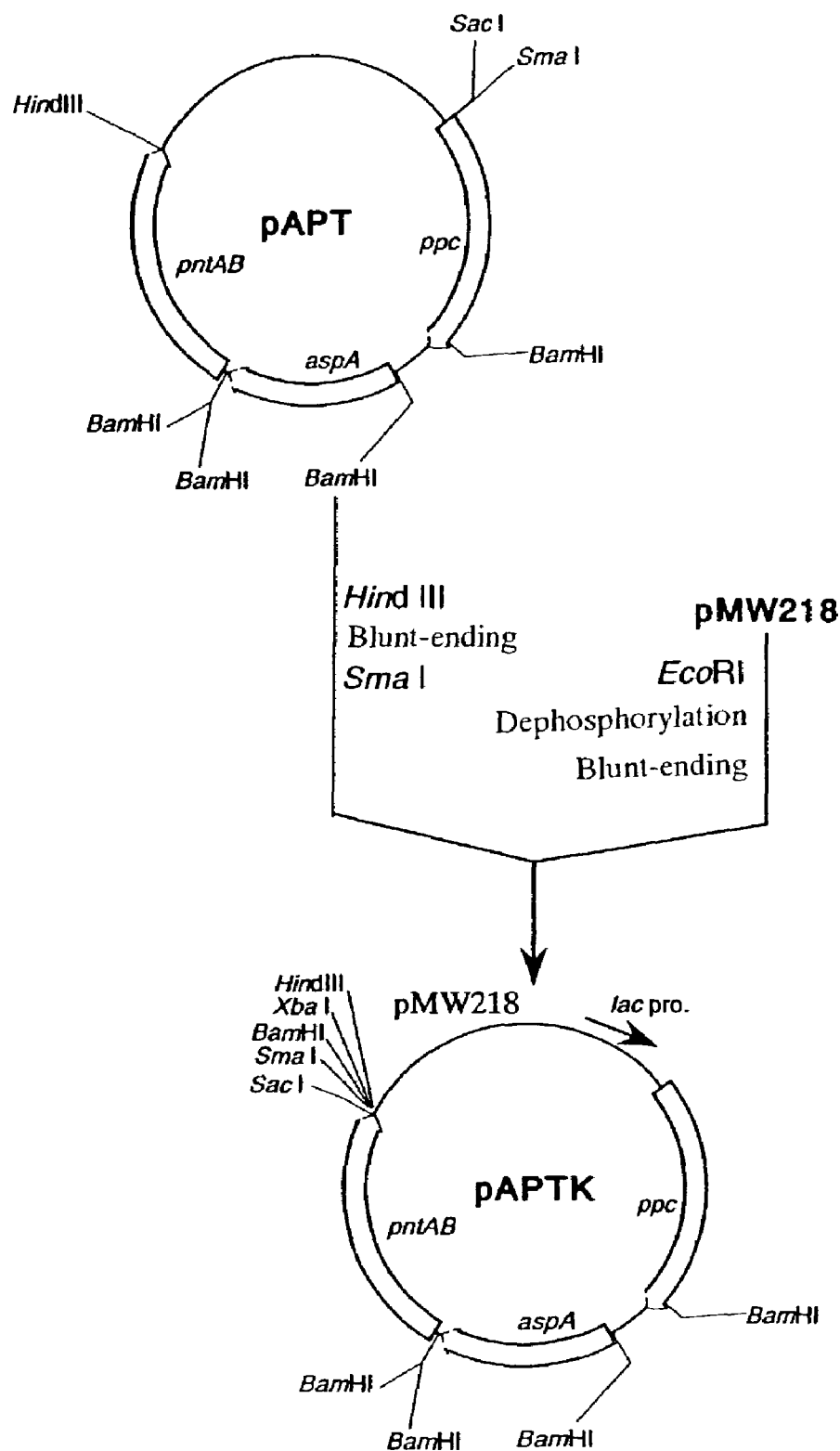
FIG. 15 shows a production process of plasmid pAPTK containing ppc, pntAB and aspA.

The plasmid pAPT described in the aforementioned Example 3 was digested with HindIII, blunt-ended for the both ends, and further digested with SmaI to obtain a DNA fragment containing ppc, aspA and pntAB. Then, pMW218 (Nippon Gene) was digested with EcoRI and blunt-ended for the both ends, and the previously obtained DNA fragment containing ppc, aspA and pntAB was inserted into the blunt-ended EcoRI cleavage site to obtain pAPTK (FIG. 15).

Figure 16:
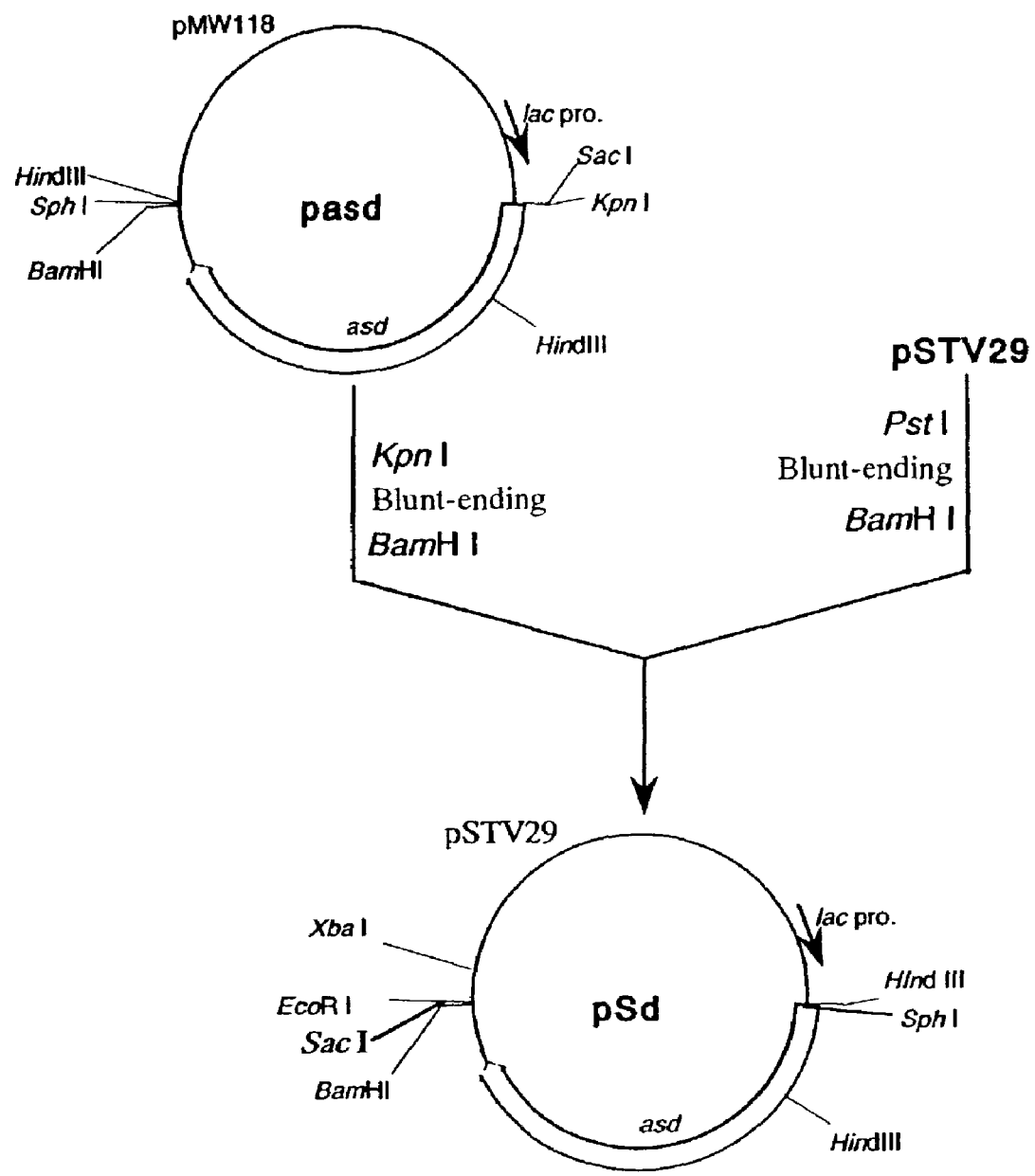
FIG. 16 shows a production process of the plasmid pSd containing asd.

Then, pasd described in International Publication No. WO95/16042 was digested with KpnI, blunt-ended for the both ends, and further digested with BamHI to obtain a DNA fragment containing asd. Then, pSTV29 was digested with PstI, blunt-ended for the both ends, and inserted with the previously obtained asd fragment at the BamHI cleavage site to obtain pSd (FIG. 16).

Figure 17:
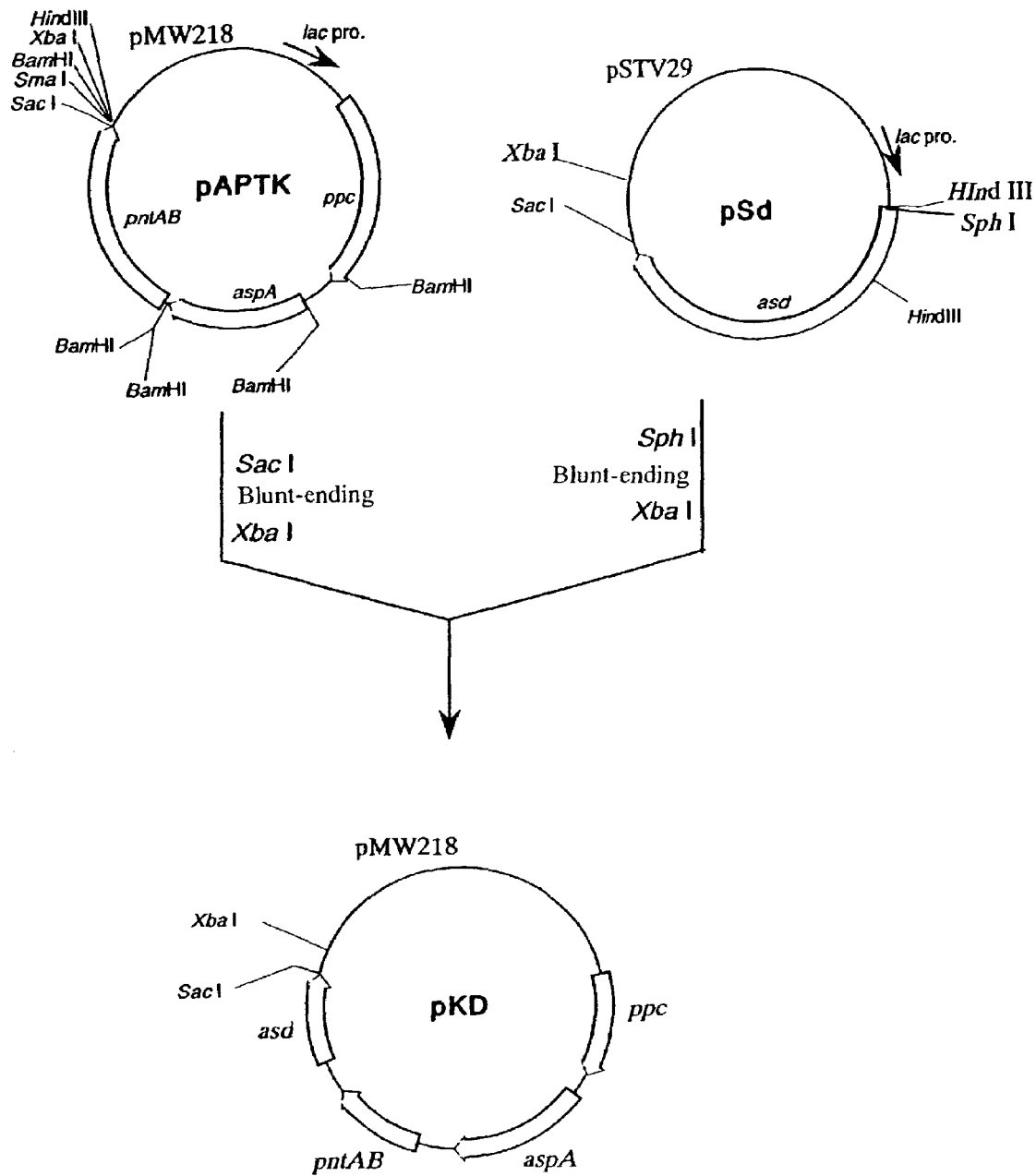
FIG. 17 shows a production process of the plasmid pKD containing ppc, pntAB, aspA and asd.

Then, pSd was digested with SphI, blunt-ended for the both ends, and further digested with XbaI to obtain a DNA fragment containing asd again. Then, pAPTK was digested with SadI and blunt-ended for the both ends, and the previously obtained asd fragment was inserted at the XbaI cleavage site to obtain pKD (FIG. 17).

<2> Introduction of Four Kinds of Genes and Evaluation of L-Lysine Productivity To a transformant into which pCABD2, pCABD(B) or pCABDE1 was introduced, which were obtained in the aforementioned Example 1, pAPT (Reference plasmid 1), pAPTK (Reference plasmid 2) or pKD was introduced. The obtained transformants contained two kinds of plasmids, i.e. one of pAPT, pAPTK and pKD, and one of pCABD2, pCABD(B) and pCABDE1. These transformants were examined for the L-lysine productivity in the same manner as in Example 1 <2>.

The results are shown in Table 4.

TABLE 4

|  | Lys accumulation (mg/dl) |
|---|---|
| pCABD2 + pAPT | 1500 |
| pCABD2 + pAPTK | 1500 |
| pCABD2 + pKD | 1600 |
| pCABD(B) + pKD | 1590 |
| pCABDE1 + pKD | 1580 |

As clearly seen from the results shown in Table 4, when asd was enhanced together with dapA+lysC+dapB+ddh+ppc+pntAB+aspA, marked increase of the L-lysine production amount was observed. A similar result was obtained when pCABD(B) or pCABDE1 was used instead of pCABD2.

The plasmid pAPTK mentioned in Table 4 corresponded to pAPT of which drug resistance gene was changed from that for ampicillin to that for kanamycin (because the vector was changed from pMW118 to pMW218). Since pKD was prepared by inserting asd into pAPTK, it was considered that pAPTK was more suitable than pAPT as control of pKD. Therefore, the data of pAPTK is also shown. It was also confirmed that the L-lysine production amount was not influenced even if the drug resistance gene was changed.

INDUSTRIAL APPLICABILITY

The present invention provides *Escherichia* bacteria with high L-lysine productivity, and L-lysine can be obtained with a high yield by using these bacteria.

What is claimed is:

1. An *Escherichia coli* bacterium in which:
   (a) the intracellular activities of all of the following enzymes are enhanced:
      dihydrodipicolinate synthase,
      aspartokinase,
      dihydrodipicolinate reductase,
      phosphoenolpyruvate carboxylase,
      nicotinamide adenine dinucleotide transhydrogenase, and
      aspartate-semialdehyde dehydrogenase; and
   (b) the intracellular activities of at least one of the following enzymes are enhanced:
      i) diaminopimelate dehydrogenase, or
      ii) tetrahydrodipicolinate succinylase and succinyl-diaminopimelate deacylase,
   wherein said activities are enhanced by:
      a) introducing a promoter or promoters which are operably linked to the gene encoding the enzymes into the chromosome of said bacterium,
      b) increasing the copy number of the genes encoding the enzymes by introducing one or more expression vectors into said bacterium, or
      c) combinations thereof.

2. The bacterium of claim 1, wherein intracellular activity of aspartase is enhanced.

3. The bacterium of claim 1, wherein said promoter or promoters are selected from the group consisting of lac, trp, tac, trc, and PL.

4. The bacterium of claim 1, wherein said activities are enhanced by increasing the copy number of the genes encoding the enzymes by introducing one or more expression vectors into said bacterium.

5. The bacterium of claim 1, wherein said activities are enhanced by introducing a promoter or promoters which are operably linked to the gene encoding the enzymes, wherein said promoter or promoters are selected from the group consisting of lac, trp, tac, trc, and PL, into the chromosome of said bacterium.

6. An *Escherichia coli* bacterium comprising one or more expression vectors comprising
   (a) genes encoding all of the following:
      dihydrodipicolinate synthase,
      aspartokinase,
      dihydrodipicolinate reductase,
      phosphoenolpyruvate carboxylase,
      nicotinamide adenine dinucleotide transhydrogenase, and
      aspartate-semialdehyde dehydrogenase, and
   (b) a gene encoding at least one of the following:
      i) diaminopimelate dehydrogenase, or
      ii) tetrahydrodipicolinate succinylase and succinyl-diaminopimelate deacylase.

7. The bacterium of claim 6, wherein said expression vectors further comprise a gene encoding for aspartase.

8. A method of producing L-lysine comprising culturing the bacterium of claim 1 in a medium, allowing L-lysine to accumulate, and collecting L-lysine from the culture.

9. A method of producing L-lysine comprising culturing the bacterium of claim 6 in a medium, allowing L-lysine to accumulate, and collecting L-lysine from the culture.

10. A method of producing L-lysine comprising culturing the bacterium of claim 2 in a medium, allowing L-lysine to accumulate, and collecting L-lysine from the culture.

11. A method of producing L-lysine comprising culturing the bacterium of claim 3 in a medium, allowing L-lysine to accumulate, and collecting L-lysine from the culture.

12. A method of producing L-lysine comprising culturing the bacterium of claim 4 in a medium, allowing L-lysine to accumulate, and collecting L-lysine from the culture.

13. A method of producing L-lysine comprising culturing the bacterium of claim 5 in a medium, allowing L-lysine to accumulate, and collecting L-lysine from the culture.

14. A method of producing L-lysine comprising culturing the bacterium of claim 7 in a medium, allowing L-lysine to accumulate, and collecting L-lysine from the culture.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: Primer for amplification of a promoter portion
      of tet

<400> SEQUENCE: 1
tcaagaattc tcatgtttga                                                 20

<210> SEQ ID NO 2
<211> LENGTH: 35
<212> TYPE: DNA
<213> ORGANISM: Artificial
<220> FEATURE:
<223> OTHER INFORMATION: Primer for amplification of a promoter portion
      of tet

<400> SEQUENCE: 2
gttagatttg gtacccggtg cctgactgcg ttagc                                35

<210> SEQ ID NO 3
<211> LENGTH: 30
<212> TYPE: DNA
<213> ORGANISM: Artificial
<220> FEATURE:
<223> OTHER INFORMATION: Primer for amplification of dapA

<400> SEQUENCE: 3
ggttgtggta cccccaaatg agggaagaag                                      30

<210> SEQ ID NO 4
<211> LENGTH: 20
<212> TYPE: DNA
<213> ORGANISM: Artificial
<220> FEATURE:
<223> OTHER INFORMATION: Primer for amplification of dapA

<400> SEQUENCE: 4
tggaacctct gttgctgcag                                                 20

<210> SEQ ID NO 5
<211> LENGTH: 20
<212> TYPE: DNA
```

```
<213> ORGANISM: Artificial
<220> FEATURE:
<223> OTHER INFORMATION: Primer for amplification of aspA

<400> SEQUENCE: 5
tgatcagcga aacactttta                                           20

<210> SEQ ID NO 6
<211> LENGTH: 19
<212> TYPE: DNA
<213> ORGANISM: Artificial
<220> FEATURE:
<223> OTHER INFORMATION: Primer for amplification of aspA

<400> SEQUENCE: 6
cagcaaacta tgatgagaa                                            19
```